United States Patent
Hull et al.

(10) Patent No.: US 11,793,623 B1
(45) Date of Patent: Oct. 24, 2023

(54) SYSTEMS AND METHODS FOR PERCUTANEOUSLY PLACING BIOLOGIC GRAFTS AT A PROCEDURAL SITE

(71) Applicant: Avenu Medical, Inc., San Juan Capistrano, CA (US)

(72) Inventors: Jeffrey E. Hull, Midlothian, VA (US); Justin K. Mann, Dana Point, CA (US); Mark A. Ritchart, Dana Point, CA (US)

(73) Assignee: AVENU MEDICAL, INC, San Juan Capistrano, CA (US)

( * ) Notice: Subject to any disclaimer, the term of this patent is extended or adjusted under 35 U.S.C. 154(b) by 460 days.

(21) Appl. No.: 17/070,787

(22) Filed: Oct. 14, 2020

Related U.S. Application Data

(60) Provisional application No. 62/914,729, filed on Oct. 14, 2019.

(51) Int. Cl.
| | |
|---|---|
| *A61F 2/06* | (2013.01) |
| *A61B 18/04* | (2006.01) |
| *A61M 25/09* | (2006.01) |
| *A61B 17/11* | (2006.01) |
| *A61B 18/00* | (2006.01) |

(Continued)

(52) U.S. Cl.
CPC ............... *A61F 2/06* (2013.01); *A61B 18/04* (2013.01); *A61B 17/3468* (2013.01); *A61B 2017/1107* (2013.01); *A61B 2018/00601* (2013.01); *A61M 25/0668* (2013.01); *A61M 25/09* (2013.01)

(58) Field of Classification Search
CPC .... A61F 2/06; A61F 2/064; A61F 2/07; A61F 2/966; A61M 25/0169; A61M 25/0194; A61M 25/0172; A61M 25/06–0612; A61M 2025/0197; A61M 25/0102; A61M 25/0662; A61M 25/09041; A61M 25/0108; A61M 1/3655; A61M 2025/0095; A61M 2025/0266; A61B 17/11; A61B 17/3415; A61B 17/3468; A61B 2017/1107; A61B 2017/1135; A61B 2017/00292

See application file for complete search history.

(56) References Cited

U.S. PATENT DOCUMENTS

| | | |
|---|---|---|
| 9,452,015 B2 | 9/2016 | Kellerman et al. |
| 2002/0049403 A1 * | 4/2002 | Alanis ...................... A61F 2/06 623/1.36 |

(Continued)

FOREIGN PATENT DOCUMENTS

WO WO-2021221607 A1 * 11/2021

*Primary Examiner* — Erich G Herbermann
*Assistant Examiner* — Linnae E. Raymond
(74) *Attorney, Agent, or Firm* — Stinson LLP

(57) ABSTRACT

A catheter having opposed tissue contacting surfaces for creating an anastomosis between two blood vessels is utilized to facilitate a method for percutaneously placing a biologic graft at a procedural site. The method may comprise steps of inserting a guidewire into a blood vessel, placing a sheath over the guidewire, advancing a biologic graft over the guidewire into the blood vessel at a biologic graft attachment site, advancing a catheter over the guidewire, pushing a distal tip of the catheter through the biologic graft, a vessel wall of the blood vessel, and into a lumen of the blood vessel, and creating an anastomosis between the biologic graft and the blood vessel by activating the catheter to apply energy to the vessel wall and to a wall of the biologic graft.

20 Claims, 26 Drawing Sheets

(51) Int. Cl.
*A61M 25/06* (2006.01)
*A61B 17/34* (2006.01)

(56) References Cited

U.S. PATENT DOCUMENTS

| | | | | |
|---|---|---|---|---|
| 2006/0111698 | A1* | 5/2006 | Kwon | A61B 17/00491 |
| | | | | 606/8 |
| 2017/0049450 | A1* | 2/2017 | Foerster | A61B 18/082 |
| 2018/0185563 | A1* | 7/2018 | Pillai | A61M 25/0102 |
| 2018/0333203 | A1* | 11/2018 | Kellerman | A61M 25/0108 |

* cited by examiner

SYSTEMS AND METHODS FOR PERCUTANEOUSLY PLACING BIOLOGIC GRAFTS AT A PROCEDURAL SITE

This application claims the benefit under 35 U.S.C. 119(e) of the filing date of Provisional U.S. Application Ser. No. 62/914,729, entitled Systems and Methods for Percutaneously Placing Biologic Grafts at a Procedural Site, filed on Oct. 14, 2019, which application is expressly incorporated herein by reference, in its entirety.

BACKGROUND OF THE INVENTION

Effective vascular access is necessary for many medical procedures. One such procedure, performed on a repeated, regular basis on patients with compromised kidney function, is hemodialysis treatment. The number of patients diagnosed with kidney disease currently increases at a rate of 5-7% per year.

Successful hemodialysis treatment is only possible with well-functioning vascular access. In state of the art approaches, an Arterio-Venous Fistula (AVF) is a primary choice for many hemodialysis cases. Such AVF's are described, for example, in the assignee's U.S. Pat. No. 9,452,015, which is expressly incorporated herein by reference, in its entirety. However, such fistulas face an increasing risk of non-maturation for patent's having certain risk factors which cause a high primary autogenous AVF failure rate, such as being aged over 65, having Coronary Artery Disease (CAD), having poor vessel distensibility, having Peripheral Vascular Disease (PVD), being diabetic, having small vein diameter, or having a history of drug abuse. Depending upon the risk of non-maturation, and other patient factors, an Arterio-Venous Graft (AVG) may be the best access option.

An AVG is placed using, typically, a biologic graft, such as an allograft or an autograft, including those comprised of cellular tissue grown and developed outside of the human body, such as those manufactured and sold by Humacyte, Inc. Other suitable graft material may comprise artificial grafts such as the FLIXENE™ AV access graft available from Getinge, as well as any other suitable available grafts.

While existing AVG placement methods typically require open surgical procedures, it would be advantageous to be able to place such grafts percutaneously, thereby reducing surgical trauma to the patient, reducing cost and complexity, and permitting a much faster and easier patient recovery as well as significantly faster usability of the AVG.

SUMMARY OF THE INVENTION

The present invention utilizes a new catheter technology to facilitate a method for percutaneously placing a biologic graft at a procedural site. For example, in one aspect of the invention, a method of placing an arteriovenous graft in a patient comprises steps of advancing a needle into a first blood vessel, preferably a vein, advancing a guidewire through the needle and into the first blood vessel, removing the needle, performing a blunt dissection between two incisions, placing a first sheath between the two incisions, backloading the guidewire through the first sheath, advancing the first sheath into the first blood vessel over the guidewire, and inserting a second guidewire into a second blood vessel, preferably an artery. Additional inventive steps include placing a second tear-away sheath over the second guidewire, advancing a biologic graft over the second guidewire into the second blood vessel at a biologic graft attachment site, advancing a catheter over the second guidewire, pushing a distal tip of the catheter through the biologic graft, a vessel wall of the second blood vessel, and into a lumen of the second blood vessel, and creating an anastomosis between the biologic graft and the second blood vessel by activating the catheter to apply energy to the vessel wall and to a wall of the biologic graft.

In illustrated embodiments, the two incision comprise first and second incisions, the first incision being disposed to access the vein and the second incision being disposed to access the artery. The catheter, in illustrated embodiments, comprises the distal tip and a proximal portion, each of the distal tip and the proximal portion having corresponding tissue contacting surfaces, wherein the distal tip pushing step includes pushing the distal tip distally relative to the catheter proximal portion, so that the tissue contacting surface of the distal tip is disposed in the lumen of the artery and the tissue contacting surface of the proximal portion is disposed proximally of the artery wall and the biologic graft wall.

The creating an anastomosis step comprises withdrawing the distal tip of the catheter proximally so that the artery wall and the biologic graft wall are clamped between the respective tissue contacting surfaces. A thermal energy element disposed on at least one of the respective tissue contacting surfaces is energized, the energized thermal energy element then cutting the artery wall and the biologic graft wall to create the anastomosis between the artery and the biologic graft. A ligature is placed at the anastomosis site to secure the biologic graft and the artery and to maintain hemostasis.

The biologic graft, as illustrated, comprises a tube sock biologic. The step of advancing the biologic graft may comprise placing the biologic graft over a third sheath. The second guidewire is poked through a closed end of the tube sock biologic graft and through the third sheath. The biologic graft and the third sheath then are advanced through the second sheath into the artery at the biologic graft attachment site. The ligature is placed at the anastomosis site by using a push catheter to push the ligature from an open end of the biologic graft distally to the anastomosis site.

At this juncture, in some embodiments, the biologic graft may be pushed distally into the vein. The second sheath may then be placed into the biologic graft, after which a proximal end of the second guidewire is poked through a closed end of the biologic graft and the second guidewire is pushed through the second sheath. The biologic graft is then pushed in place near the anastomosis site.

In another aspect of the invention, a method comprises steps of inserting a guidewire into a blood vessel, placing a sheath over the guidewire, advancing a biologic graft over the guidewire into the blood vessel at a biologic graft attachment site, advancing a catheter over the guidewire, pushing a distal tip of the catheter through the biologic graft, a vessel wall of the blood vessel, and into a lumen of the blood vessel, and creating an anastomosis between the biologic graft and the blood vessel by activating the catheter to apply energy to the vessel wall and to a wall of the biologic graft.

The catheter preferably comprises the distal tip and a proximal portion, each of the distal tip and the proximal portion having corresponding tissue contacting surfaces, wherein the distal tip pushing step includes pushing the distal tip distally relative to the catheter proximal portion, so that the tissue contacting surface of the distal tip is disposed in the lumen of the artery and the tissue contacting surface of the proximal portion is disposed proximally of the artery wall and the biologic graft wall.

The creating an anastomosis step then may comprise withdrawing the distal tip of the catheter proximally so that the artery wall and the biologic graft wall are clamped between the respective tissue contacting surfaces. The thermal energy element, disposed on at least one of the respective tissue contacting surfaces, is energized, the energized thermal energy element cutting the artery wall and the biologic graft wall to create the anastomosis between the artery and the biologic graft. A ligature is placed at the anastomosis site to secure the biologic graft and the artery and to maintain hemostasis.

The invention, together with additional features and advantages thereof, may best be understood by referencing the following description in conjunction with the accompanying specifications.

DETAILED DESCRIPTION OF THE INVENTION

Notation and Nomenclature

Figure 1:
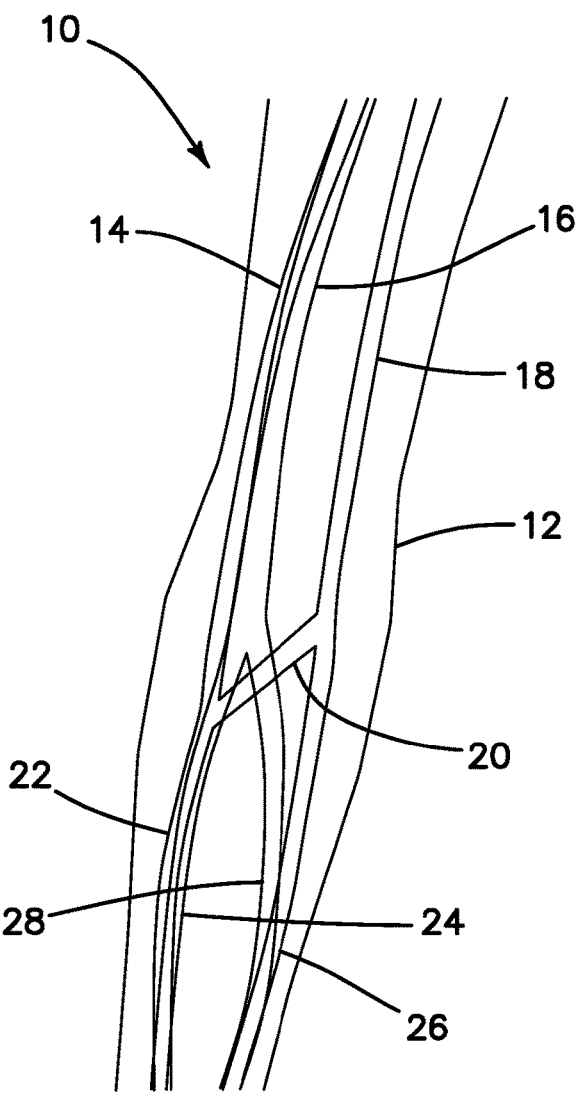
FIG. 1 is a schematic representation of the anatomy of a patient in the vicinity of a selected procedural site for placing a biologic graft percutaneously using one exemplary method performed in accordance with the principles of the present invention.

Certain terms are used throughout the following description and claims to refer to particular system components. As one skilled in the art will appreciate, companies that design and manufacture medical devices may refer to a component by different names. This document does not intend to distinguish between components that differ in name but not function.

In the following discussion and in the claims, the terms "including" and "comprising" are used in an open-ended fashion, and thus should be interpreted to mean "including, but not limited to . . . . "

Reference to a singular item includes the possibility that there are plural of the same items present. More specifically, as used herein and in the appended claims, the singular forms "a," "an," "said" and "the" include plural references unless the context clearly dictates otherwise. It is further noted that the claims may be drafted to exclude any optional element. As such, this statement serves as antecedent basis for use of such exclusive terminology as "solely," "only" and the like in connection with the recitation of claim elements, or use of a "negative" limitation. Lastly, it is to be appreciated that unless defined otherwise, all technical and scientific terms used herein have the same meaning as commonly understood by one of ordinary skill in the art to which this invention belongs.

Where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

All existing subject matter mentioned herein (e.g., publications, patents, patent application and hardware) is expressly incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

Before the various embodiments are described in detail, it is to be understood that this invention is not limited to particular variations set forth herein as various changes or modifications may be made, and equivalents may be substituted, without departing from the spirit and scope of the invention. As will be apparent to those of skill in the art upon reading this disclosure, each of the individual embodiments described and illustrated herein has discrete components and features which may be readily separated from or combined with the features of any of the other several embodiments without departing from the scope or spirit of the present invention. In addition, many modifications may be made to adapt a particular situation, material, composition of matter, process, process act(s) or step(s) to the objective(s), spirit or scope of the present invention. All such modifications are intended to be within the scope of the claims made herein.

The technology disclosed herein would have a broad application in vessel surgery for humans and other mammals. This includes surgery of ducts, ureters, arteries, veins, grafts, or any other tubular structure that transports material. Some of these procedures include, but are not limited to, artery to venous fistula creation, vascular repair, coronary artery bypass graft surgery, femoral popliteal bypass, transjugular intrahepatic portosystemic shunt, splenorenal shunt, or a mesocaval shunt.

Referring now more particularly to the drawings, FIG. 1 illustrates the anatomy of a patient in the vicinity of a procedural site for an exemplary embodiment of the inventive method and system. The drawing depicts an arm 10 of a patient, having an elbow 12, a cephalic vein 14, a brachial artery 16, a basilic vein 18, a median cubital vein 20, a radial vein 22 and radial artery 24, and an ulnar vein 26 and ulnar artery 28.

Figure 2:
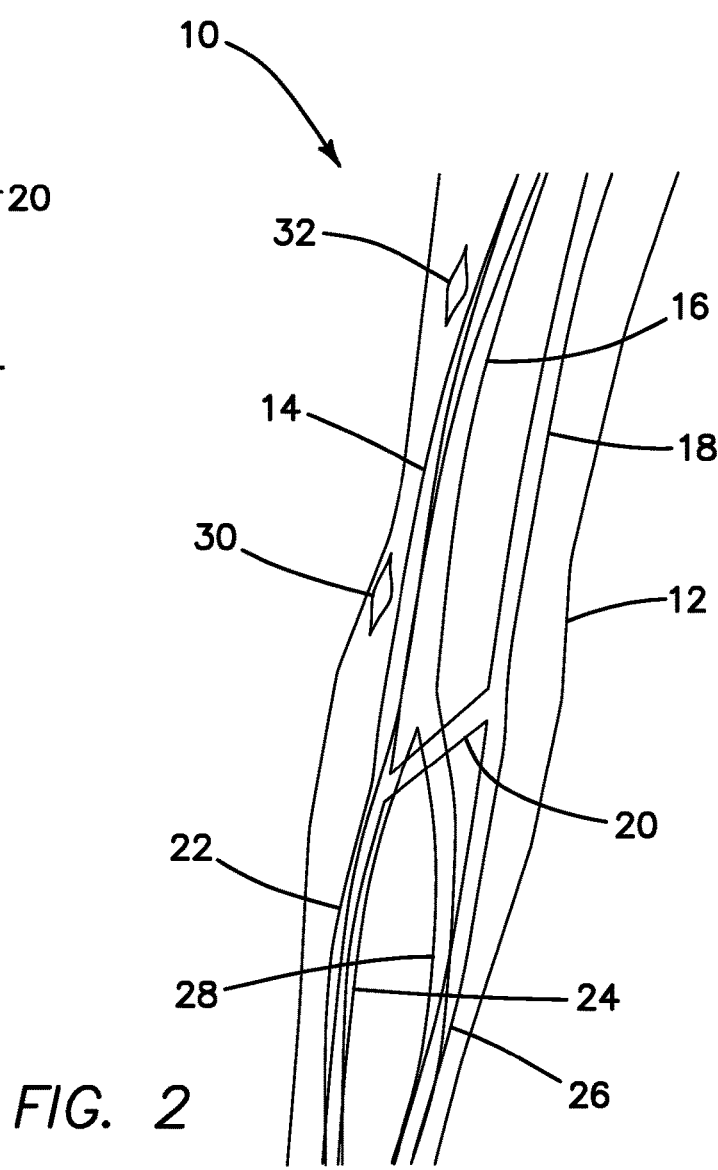
FIG. 2 is a schematic representation similar to FIG. 1, illustrating initial steps in the exemplary method.
Figure 3:
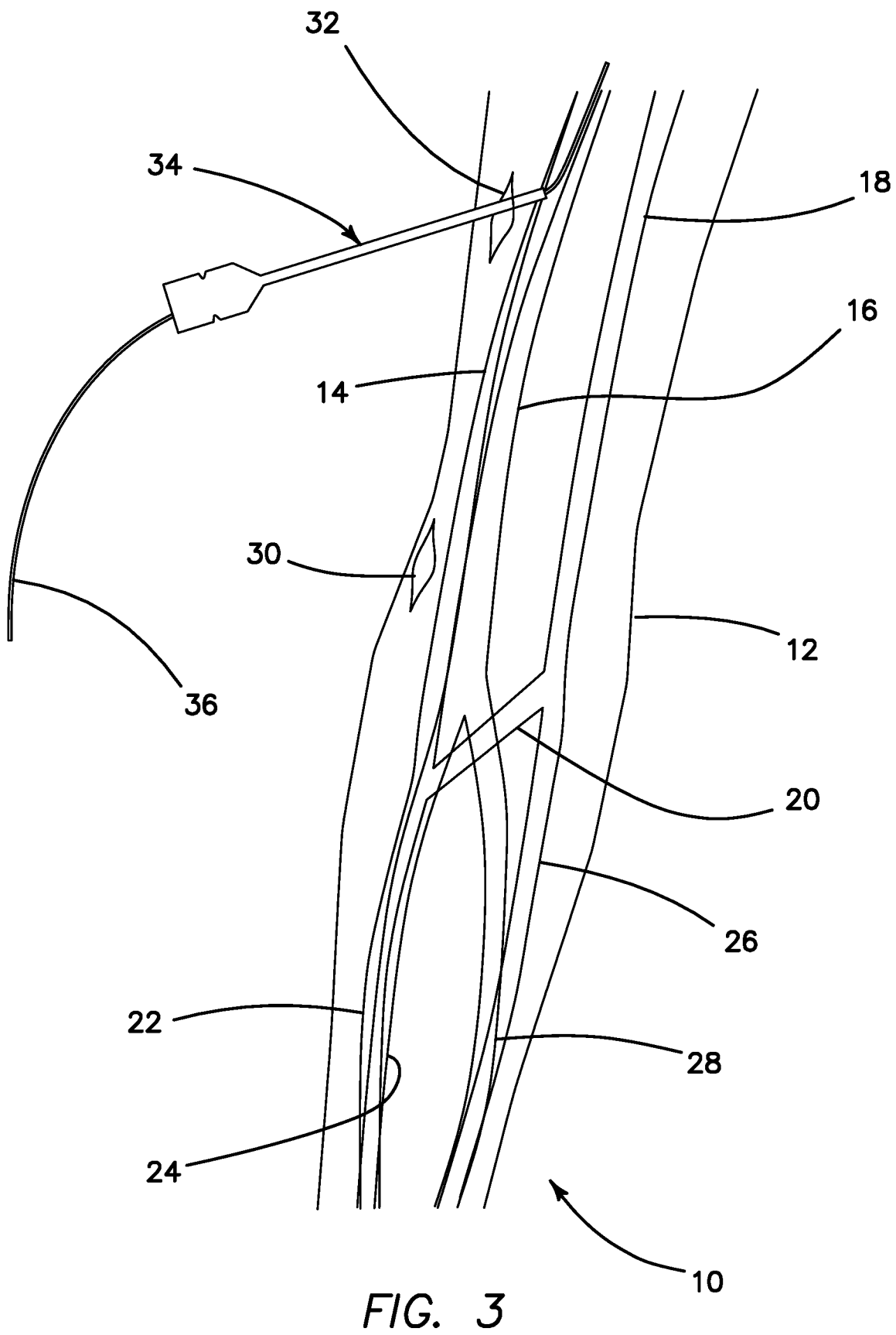
FIG. 3 is a schematic representation similar to FIG. 2, illustrating additional steps according to the exemplary method.

As shown in FIG. 2, initial steps of one exemplary method are to make a first incision 30, proximal to the elbow and near the target arterial attachment site for the graft. A second incision 32 is made proximal to the first incision 30 and near the target venous attachment site. FIG. 3 illustrates the next steps, which include advancing a crossing needle 34 or equivalent device under imaging guidance, such as ultrasound guidance, from the second incision 32 to a target venous return site in the cephalic vein 14 until venous access is attained. A guidewire 36 is then advanced through the crossing needle 34 and into the vein 14. Following this, the crossing needle 34 is removed. In exemplary embodiments, the crossing needle 34 may be a crossing needle sold under the trademark ELLIPSYS® by Avenu Medical, Inc., the assignee of the present application.

Figure 4:
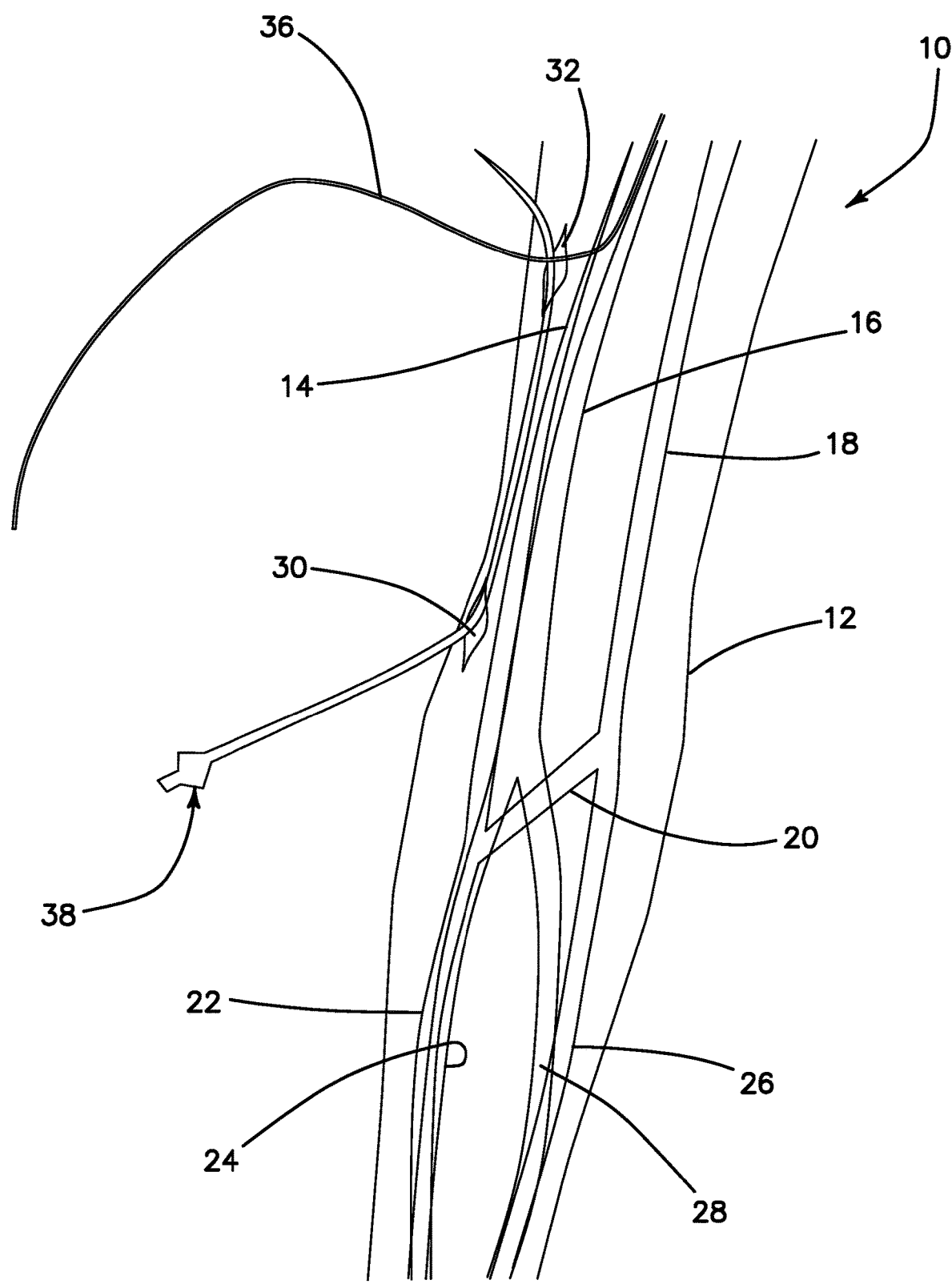
FIG. 4 is a schematic representation similar to FIGS. 2-3, illustrating additional steps according to the exemplary method.
Figure 5:
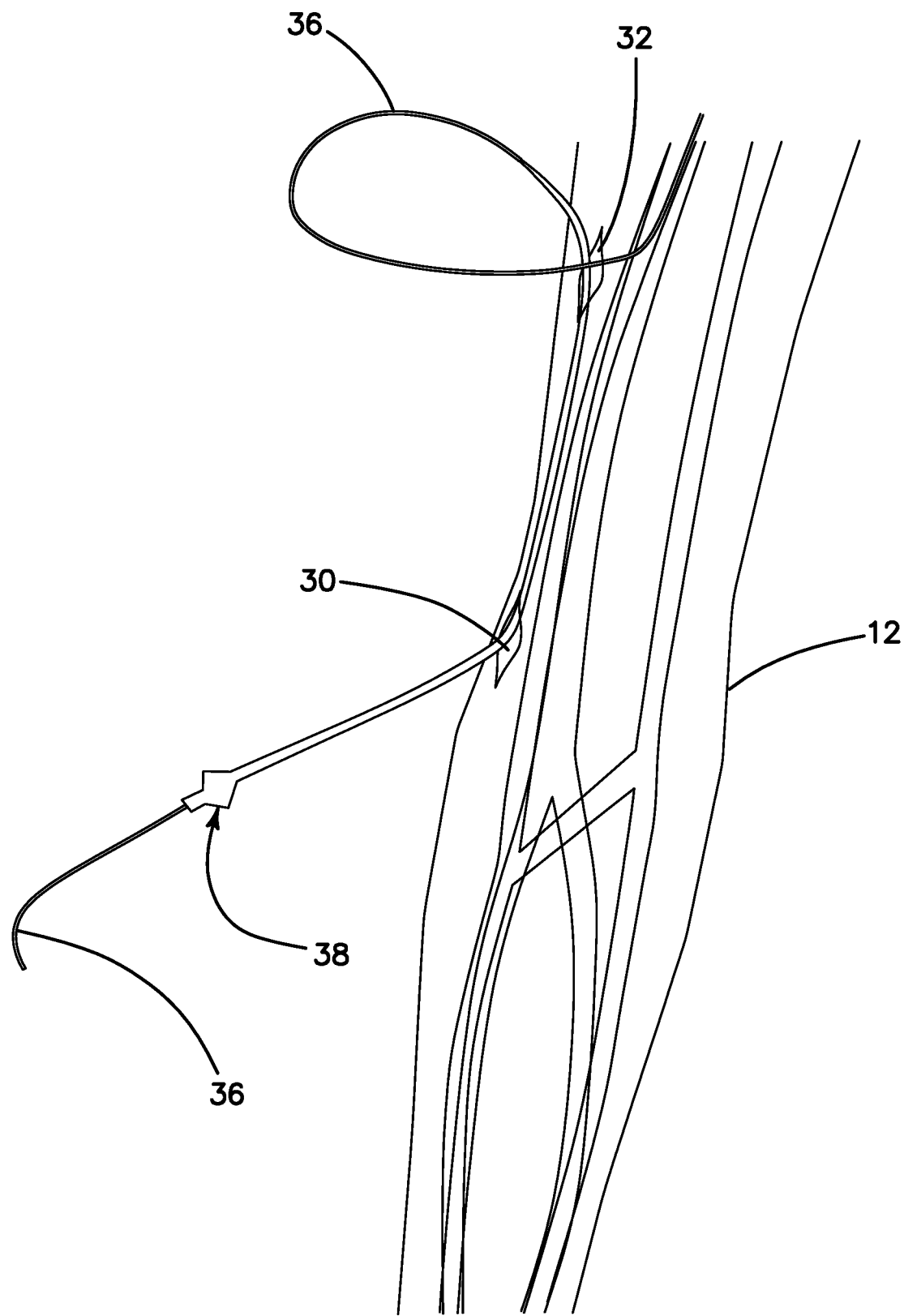
FIG. 5 is a schematic representation similar to FIGS. 2-4, illustrating additional steps according to the exemplary method.
Figure 6:
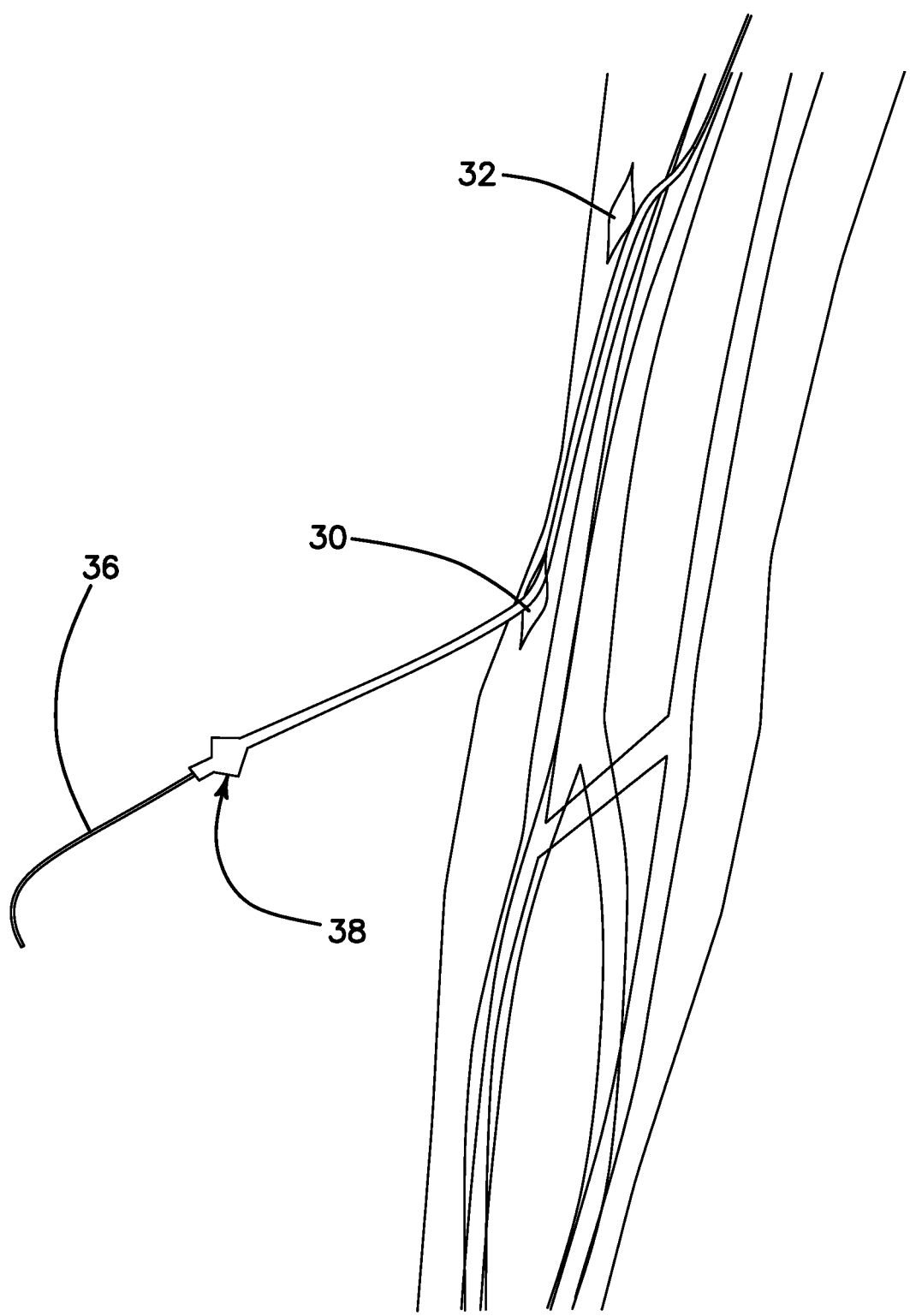
FIG. 6 is a schematic representation similar to FIGS. 2-5 illustrating additional steps according to the exemplary method.
Figure 7:
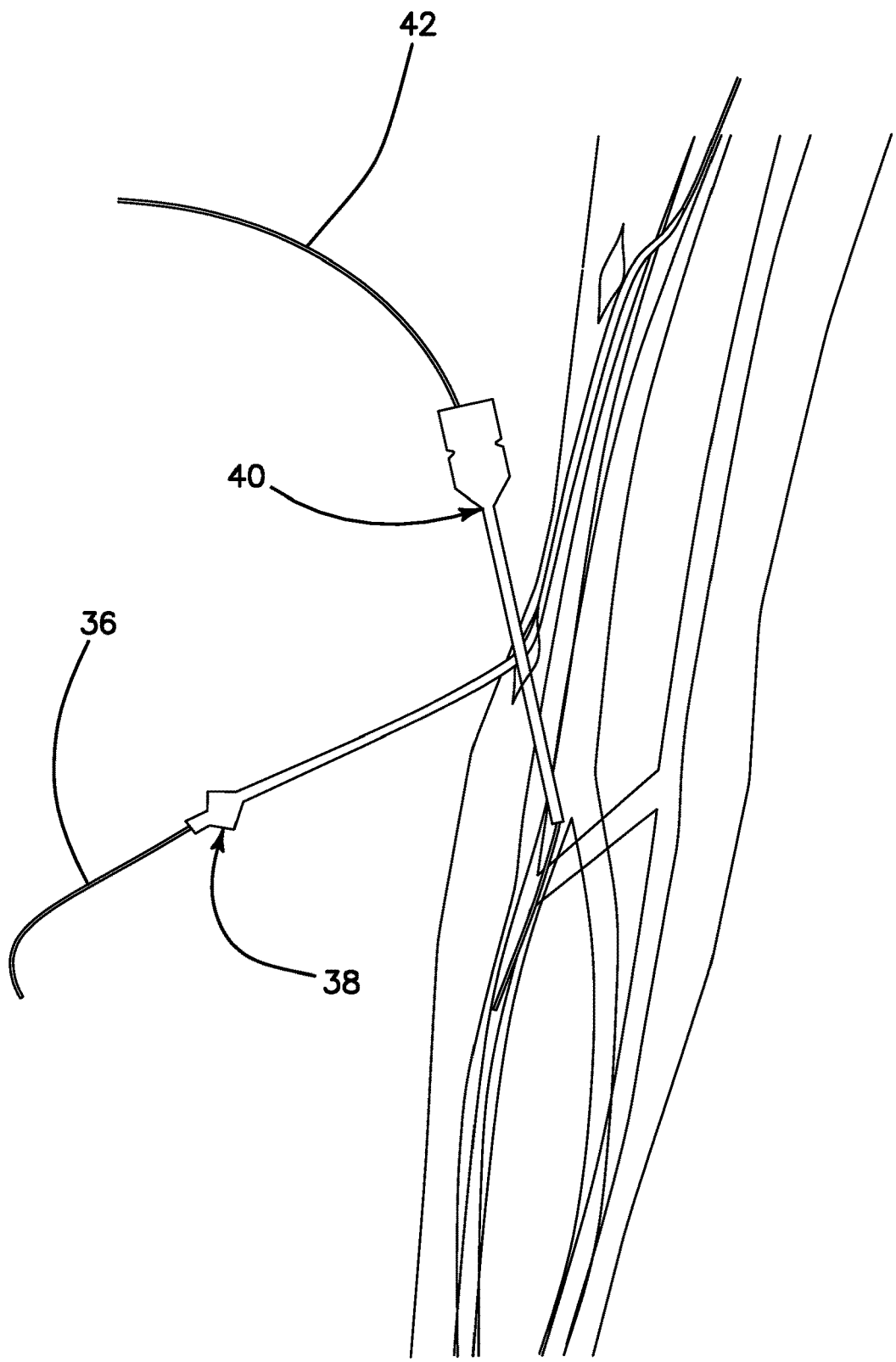
FIG. 7 is a schematic representation similar to FIGS. 2-6, illustrating additional steps according to the exemplary method.

As shown in FIG. 4, blunt dissection from the second incision 32 to the first incision 30 is performed using imaging guidance, such as ultrasound. This blunt dissection may be performed using a rod, which is pushed between tissue layers. A first tear-away sheath 38 is then placed from the first incision 30 to the second incision 32. The guidewire 36 is then back-loaded through the sheath 38, as shown in FIG. 5. The sheath 38 is then repositioned over the guidewire 36 and advanced into the target venous return site (FIG. 6). A crossing needle 40, which again may be a crossing needle sold by the present assignee, Avenu Medical, Inc., under the trademark ELLIPSYS®, is then utilized under imaging guidance, such as ultrasound, to gain arterial access at a desired fistula creation site, and a second guidewire 42 is advanced into the target vessel (FIG. 7).

Figure 8:
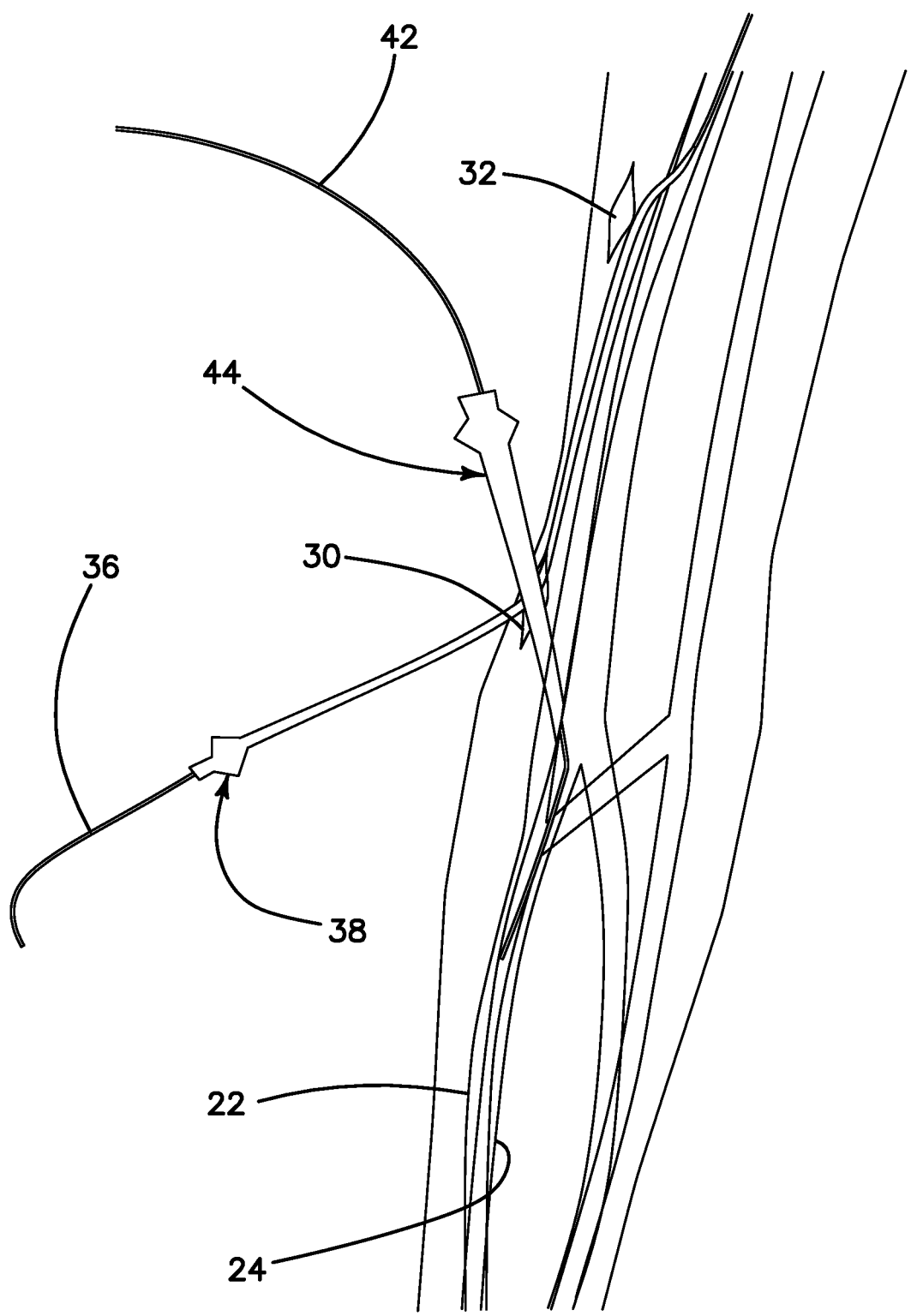
FIG. 8 is a schematic representation similar to FIGS. 2-7, illustrating additional steps according to the exemplary method.
Figure 9:
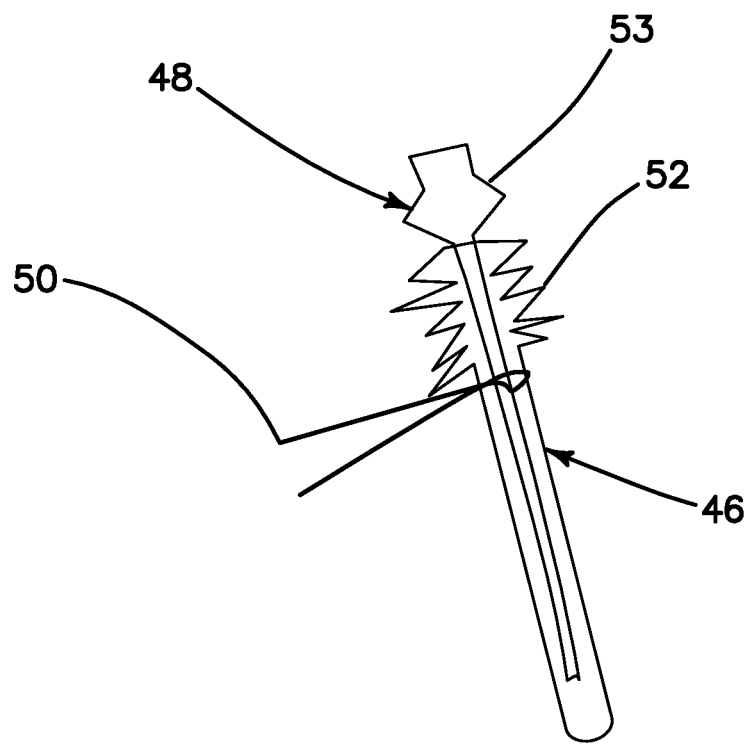
FIG. 9 is a schematic representation similar to FIGS. 2-8, illustrating additional steps according to the exemplary method.

As illustrated in FIG. 8, a second tear-away sheath 44, with a minimum 3 mm inside diameter in the exemplary embodiment, is then placed over the second guidewire 42 (the arterial access wire) and near a target artery 24. At this juncture, as shown in FIG. 9, a biologic graft 46 (tube sock biologic) is placed over a third sheath 48, which in the illustrated embodiment is a 6F 10 cm sheath. A suture or clamp (ligature) 50 may be utilized to bunch excess length 52 of the biologic graft 46 near the hemostasis valve 53.

In all embodiments and methods described herein, the term biologic graft may refer to an allograft or an autograft, including those comprised of cellular tissue grown and developed outside of the human body, such as those manufactured and sold by Humacyte, Inc. Other suitable graft material may comprise artificial grafts such as the FLIXENE™ AV access graft available from Getinge, as well as any other suitable available grafts. Such grafts are often purposed for performing coronary bypass procedures, but the inventors have found additional applications as well, as discussed herein.

Figure 10:
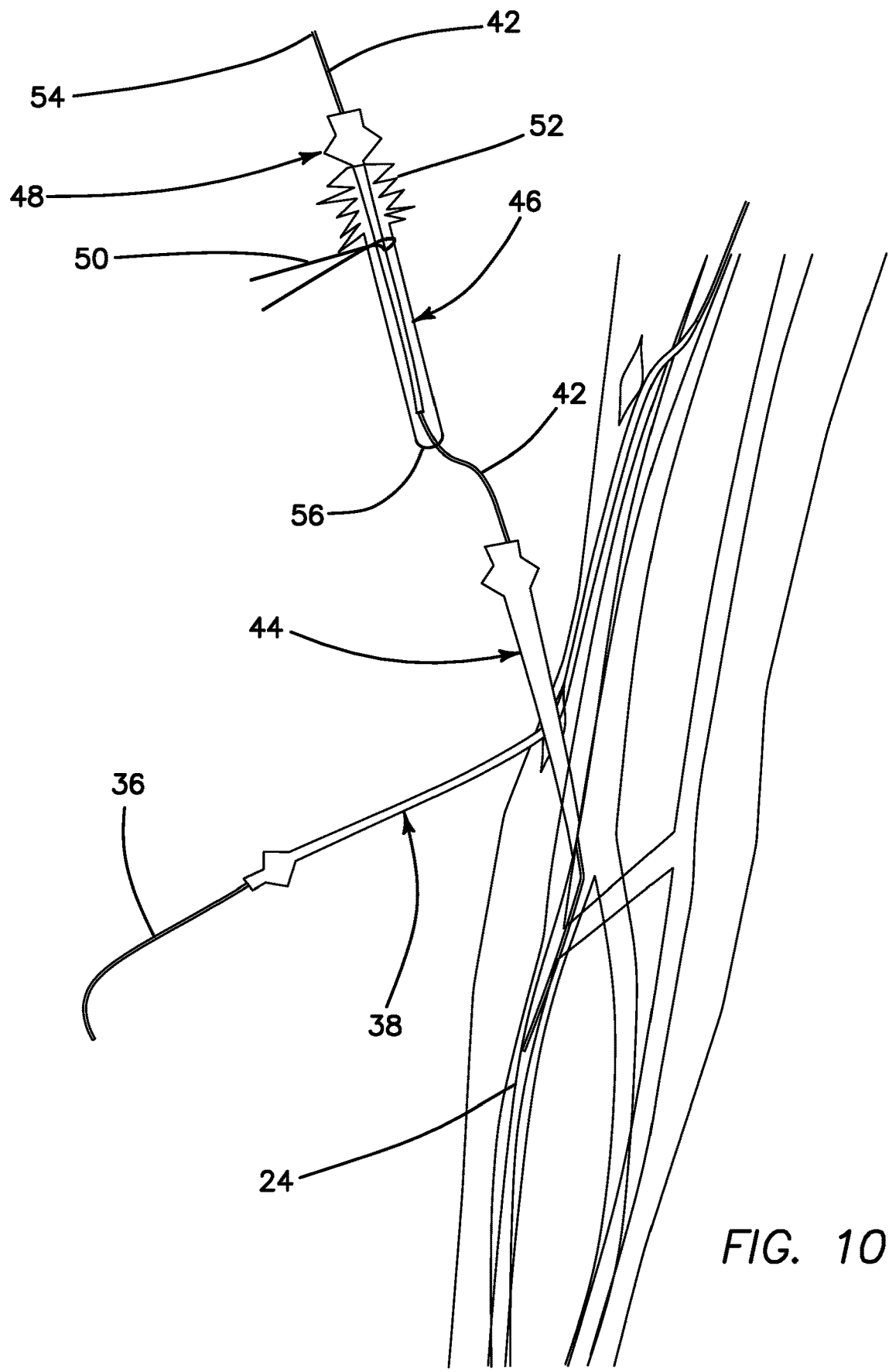
FIG. 10 is a schematic representation similar to FIGS. 2-9, illustrating additional steps according to the exemplary method.
Figure 11:
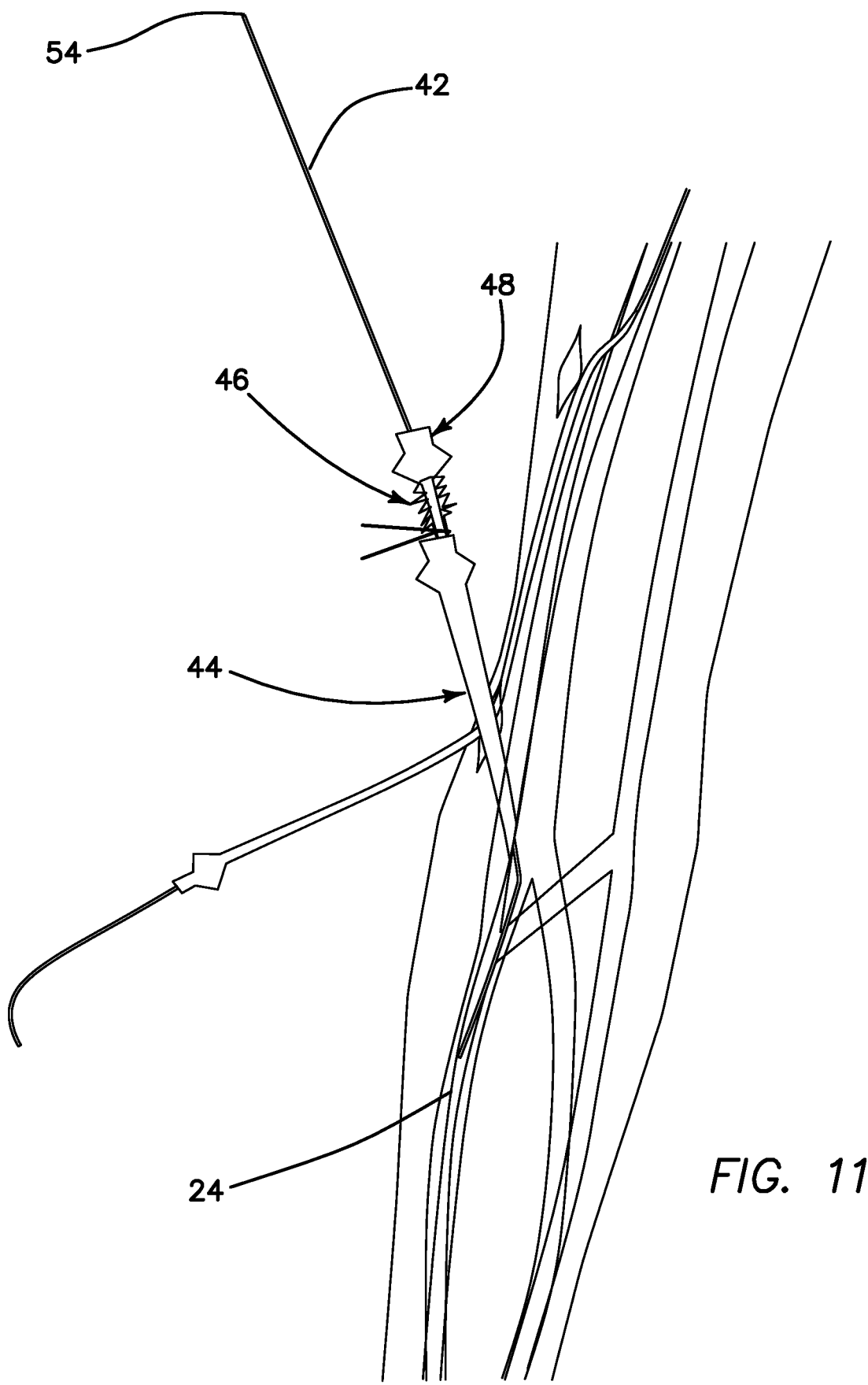
FIG. 11 is a schematic representation similar to FIGS. 2-10, illustrating additional steps according to the exemplary method.

A proximal end 54 of the second guidewire (arterial access wire) 42 is then poked through a closed end 56 of the tube sock biologic graft 46, and then through the second sheath 44, as shown in FIG. 10. In FIG. 11, it can be seen that the biologic graft 46 and the 6F (third) sheath 48 are then advanced through the second tear-away sheath 44 to the target access site in artery 24.

Figure 12:
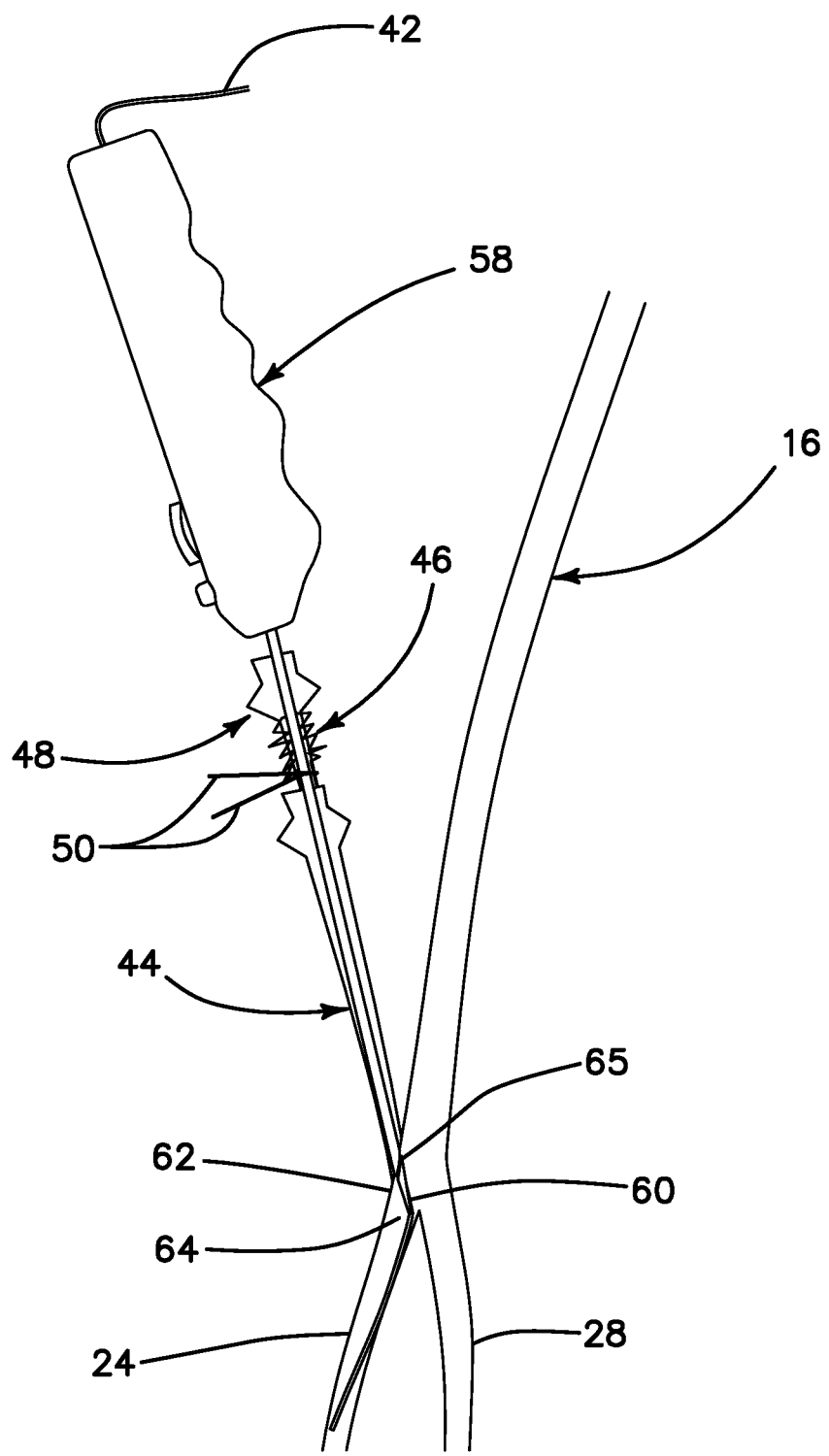
FIG. 12 is a schematic representation similar to FIGS. 2-11, illustrating additional steps according to the exemplary method.

In FIG. 12, a catheter 58, which may be a catheter sold by the assignee of the present application, Avenu Medical, Inc., under the trademark ELLIPSYS®, as described, for example, in commonly assigned U.S. Pat. No. 9,452,015 (the '015 Patent), the entire contents of which are herein expressly incorporated by reference, is advanced over the second guidewire 42. A tapered distal tip 60 of the catheter 58 is then pushed over the guidewire 42, through the biologic graft 46, an arterial wall 62 of the artery 24, and into the lumen 64 of the artery 24. The tapered tip 60 of the catheter 58 has a proximally facing tissue contacting surface, as described in the '015 Patent. The remaining portion of the catheter 58, a proximal portion, has a distally facing tissue contacting surface which corresponds to the proximally facing tissue contacting surface of the tapered distal tip 60. When the tip 60 is moved distally into the lumen 64 of the artery, the proximal portion of the catheter 58 remains in place, so that there is a spacing between the distal tip 60 and the proximal portion of the catheter 58. The catheter 58 is then latched shut, by withdrawing the distal tip 60 toward the proximal portion of the catheter 58, until the arterial wall 62 and the biologic graft 46 are clamped between the corresponding proximally and distally facing tissue contacting faces. A heating element on one or both of the proximally and distally facing tissue contacting faces is then activated (energized), thereby applying thermal energy to create an immediate and permanent anastomosis 65 between the biologic graft 46 and the artery 24. As noted above, in the illustrated embodiment, the step of latching the catheter 58 shut comprises moving the distal tip 60 proximally until tissue comprising the arterial wall 62, as well as a wall of the biologic graft 46 are clamped between the distal tip 60 and a proximal portion of the catheter 58, as described the '015 Patent. Other suitable tissue cutting approaches, well known to those of skill in the art, are within the scope of the present invention, as well. The second tear-away sheath 44 can be removed either before or after activation of the catheter 58.

Figure 13:
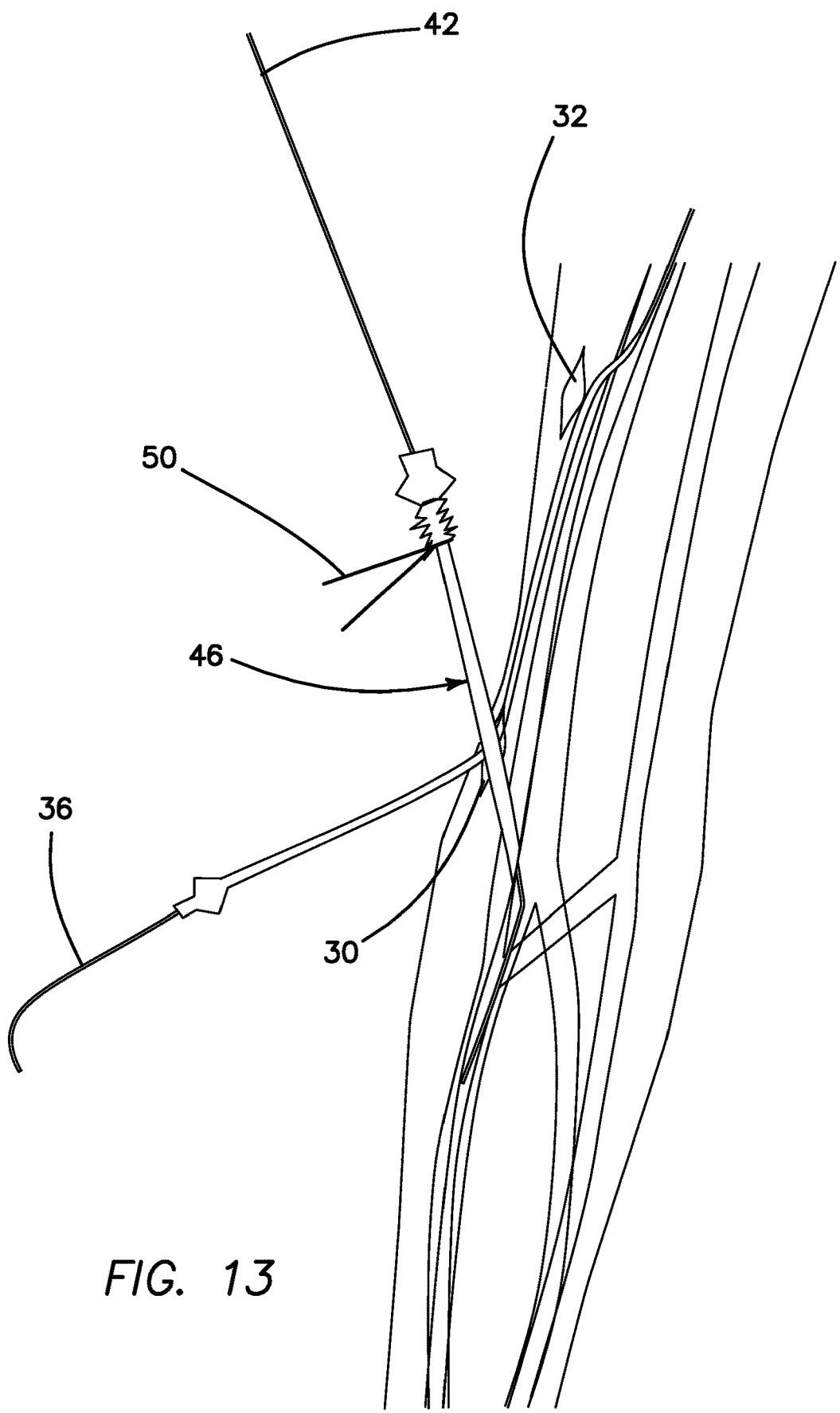
FIG. 13 is a schematic representation similar to FIGS. 2-12, illustrating additional steps according to the exemplary method.
Figure 14:
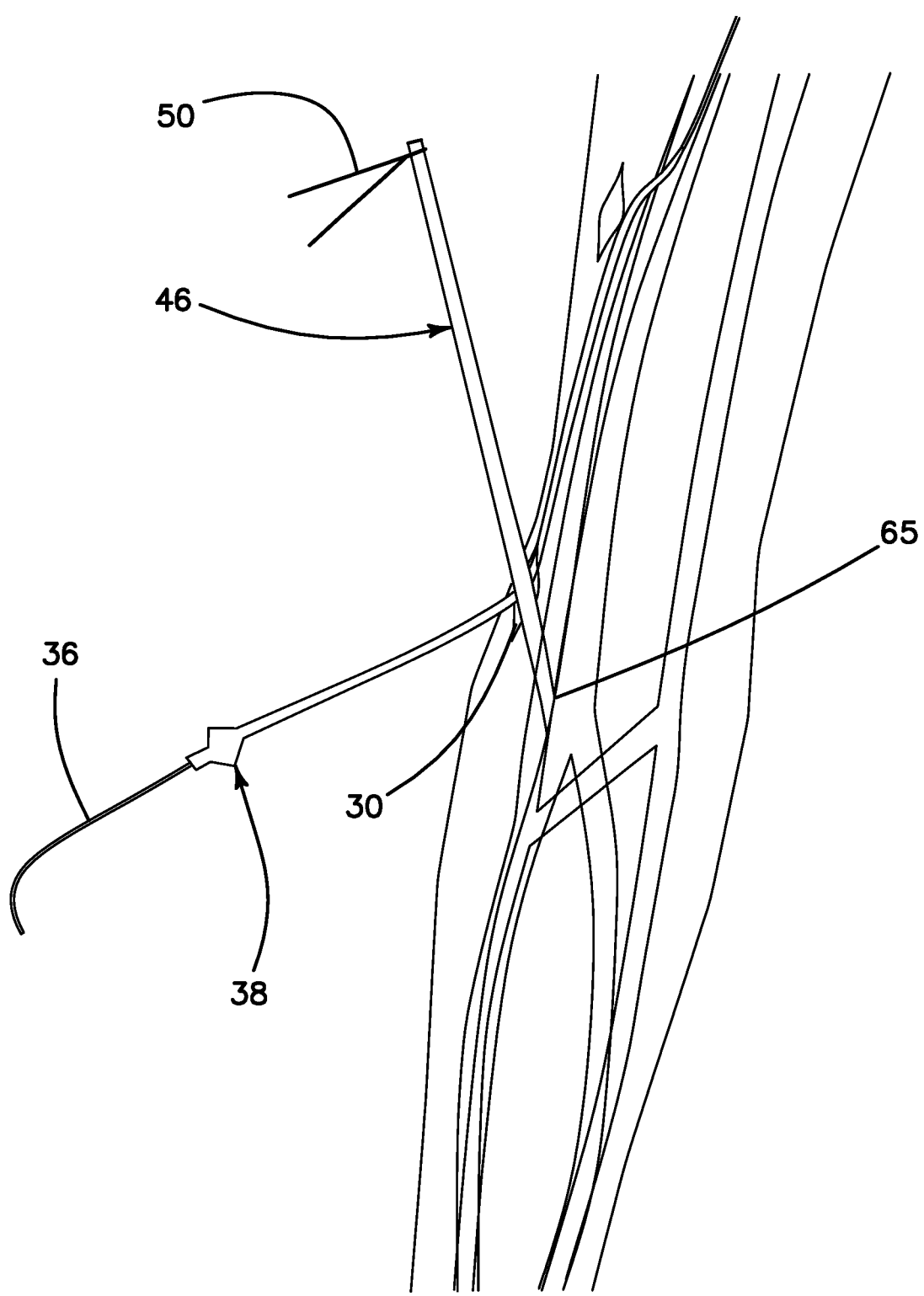
FIG. 14 is a schematic representation similar to FIGS. 2-13, illustrating additional steps according to the exemplary method.

As shown in FIG. 13, the biologic graft material 46, now permanently affixed on one end to the anastomosis 65 at the target site artery 24, is perfused with blood from the artery. The pressure in the biologic graft 46 exceeds the venous pressure, thus holding the graft 46 in place without a need for a sealing step. The arterial guidewire 42 and 6F sheath 44 can now be removed, with hemostasis being maintained by the ligature 50. With reference to FIG. 14, the ligature 50 on the open end of the biologic graft 46 can now be used in conjunction with a push catheter B (FIG. 15) to be pushed over the first guidewire 36, down the tear-away sheath 38, and into the target venous return.

Figure 15:
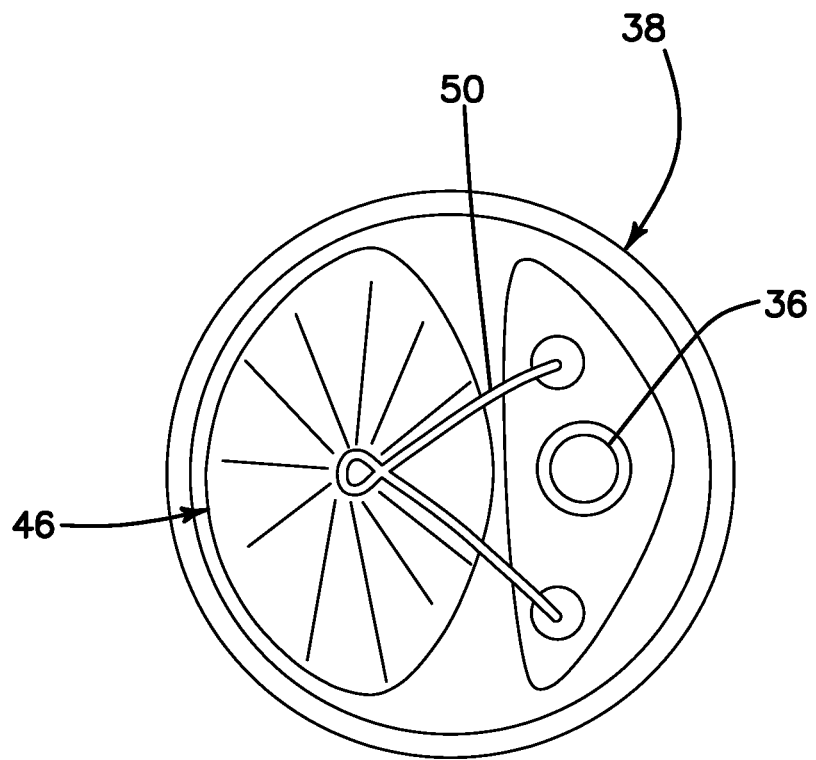
FIG. 15 is a cross-sectional view of a first sheath of an exemplary device of the invention, illustrated during performance of the step shown in FIG. 14.

FIG. 15 is a cross-sectional view of the first sheath 38, showing the lumen A of the sheath 38, the push catheter B, the first guidewire 36 (C), and ligature 50 (D), attached to the biologic graft 46(E). In the illustrated embodiment, the push catheter B is a three lumen design that enables the user to manipulate and/or extract the ligature 50 during placement of the biologic graft within the target return vein.

Figure 16:
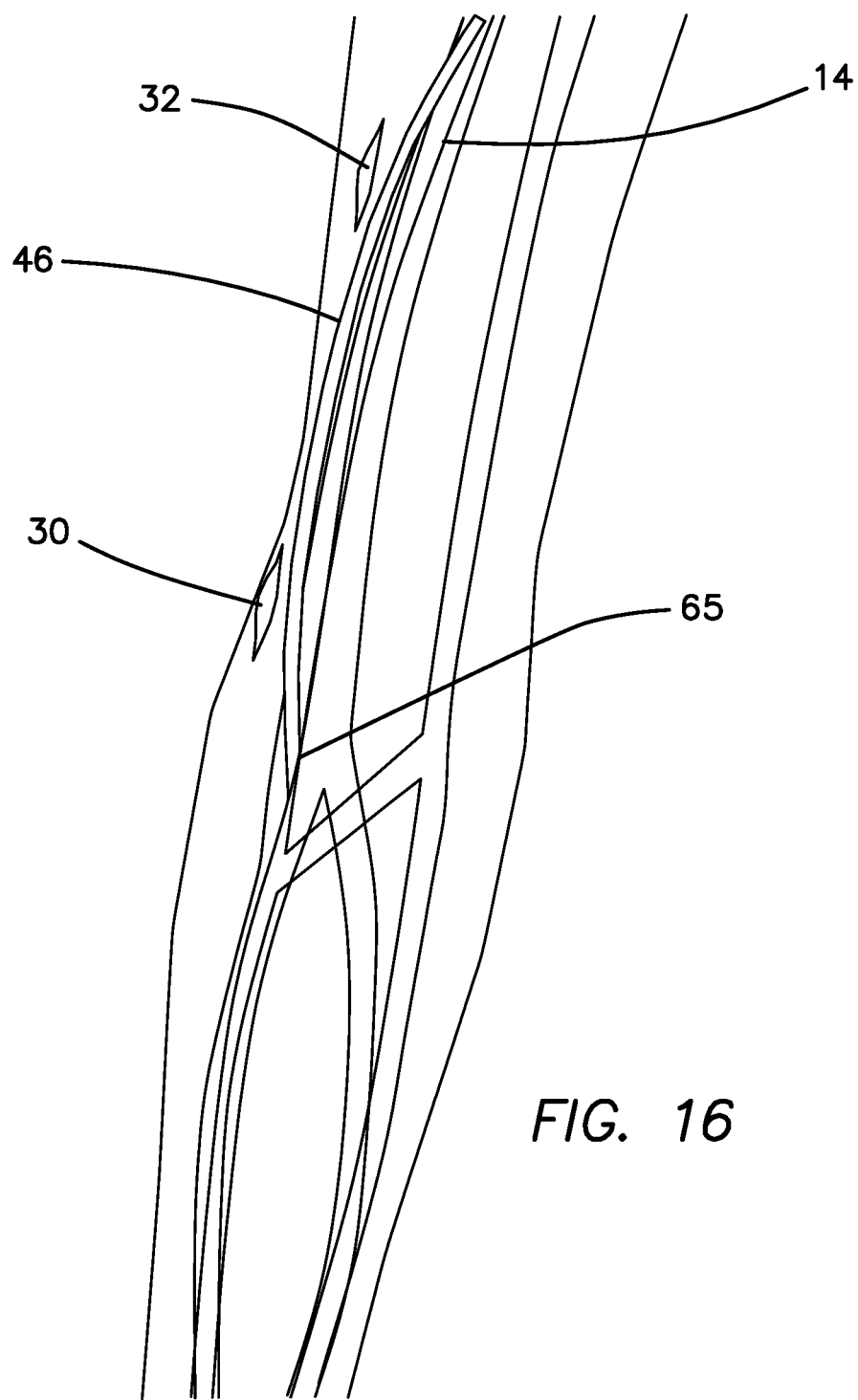
FIG. 16 is a schematic representation similar to FIGS. 2-14, illustrating a step of extracting the instruments at the conclusion of the inventive procedure.

Referring now to FIG. 16, once the biologic graft 46 is placed sufficiently far inside the vein 14 at the target return site, the first tear-away sheath 38, ligature 50, and push catheter B can be extracted.

Indications for use of methods such as those disclosed herein, involving the use of such a graft, are cases where the natural vein has been destroyed for any of various reasons, including, for example, repeated drug abuse, or perhaps such things as extensive prior medical treatments.

Figure 17:
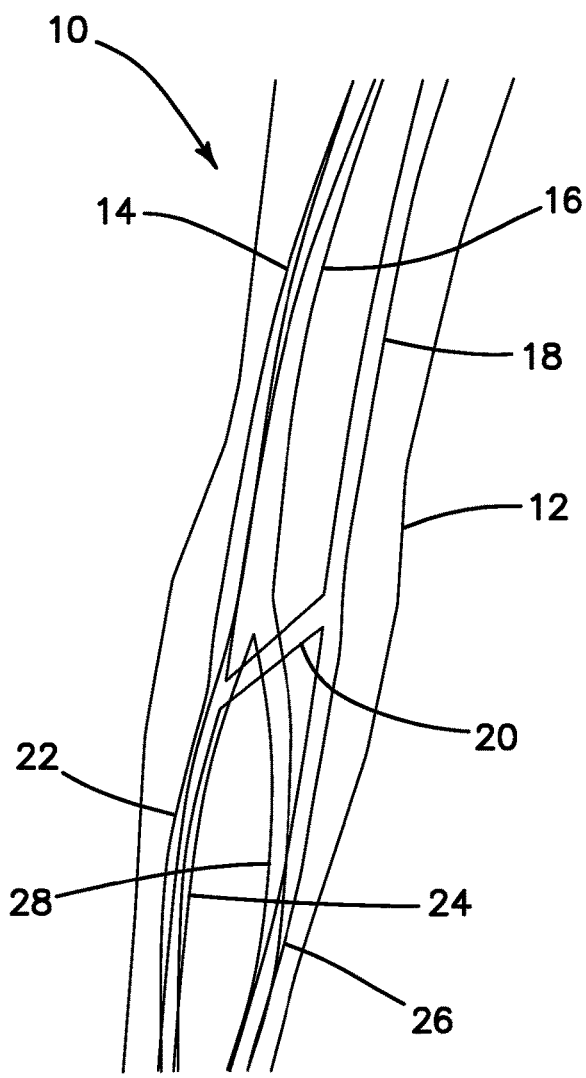
FIG. 17 is a schematic representation of the anatomy of a patient in the vicinity of a selected procedural site for placing a biologic graft percutaneously using another modified exemplary method performed in accordance with the principles of the present invention.

A second exemplary method for percutaneously placing biologic grafts at a procedural site is illustrated in FIGS. 17-30. In this method, wherein like elements are indicated using like reference numerals, FIG. 17 is similar to FIG. 1 in illustrating the anatomy of a patient in the vicinity of a procedural site. The drawing depicts an arm 10 of a patient, having an elbow 12, a cephalic vein 14, a brachial artery 16, a basilic vein 18, a median cubital vein 20, a radial vein 22 and radial artery 24, and an ulnar vein 26 and ulnar artery 28.

Figure 18:
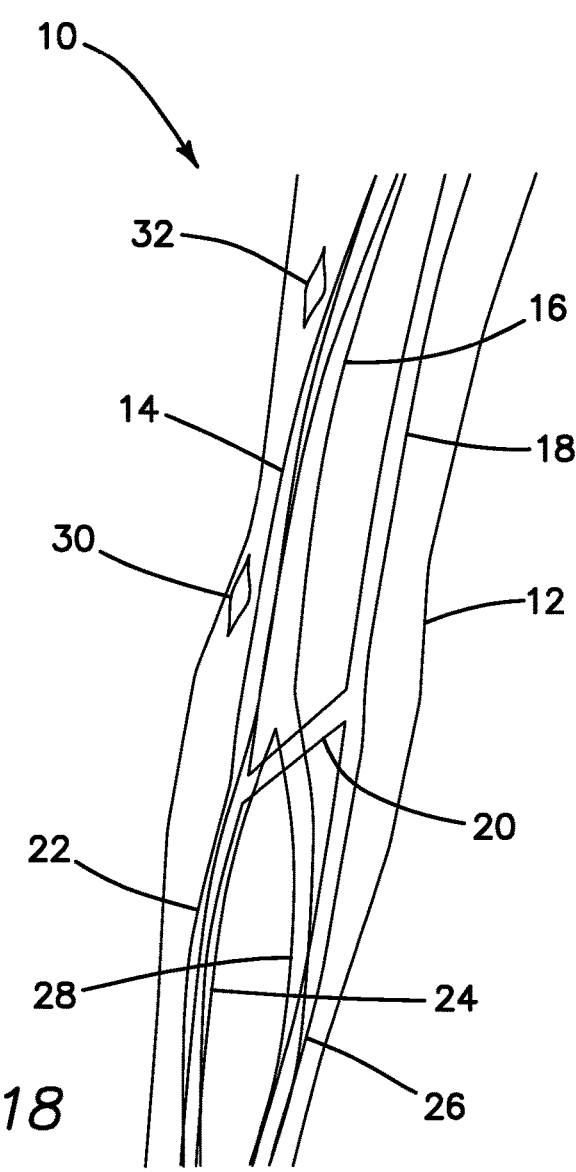
FIG. 18 is a schematic representation similar to FIG. 17, illustrating initial steps in the modified exemplary method.
Figure 19:
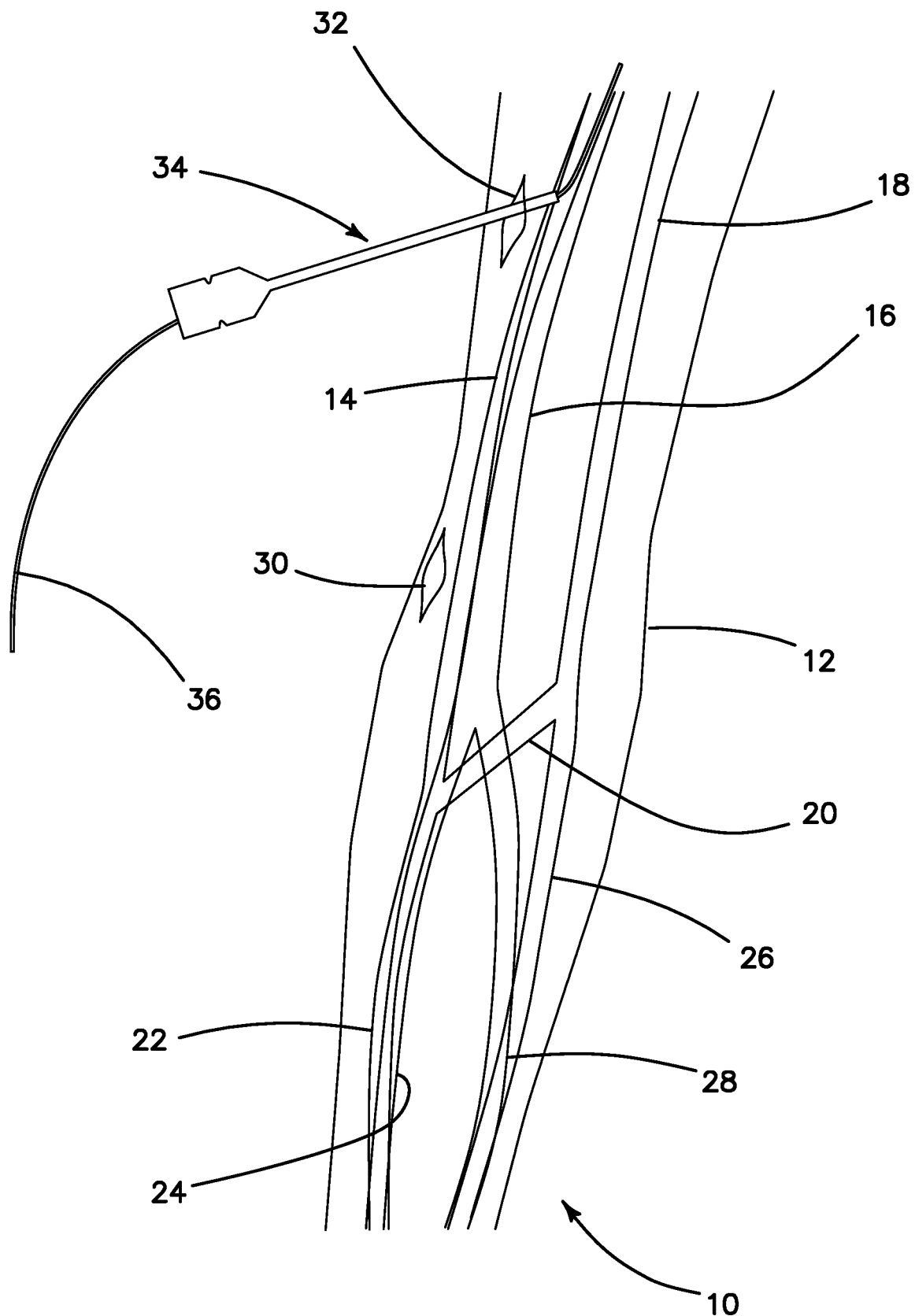
FIG. 19 is a schematic representation similar to FIG. 18, illustrating additional steps according to the modified exemplary method.

As shown in FIG. 18, initial steps of this exemplary method are to make a first incision 30, proximal to the elbow and near the target arterial attachment site for the graft. A second incision 32 is made proximal to the first incision 30 and near the target venous attachment site. FIG. 19 illustrates the next steps, which include advancing a crossing needle 34 or equivalent device under imaging guidance, such as ultrasound guidance, from the second incision 32 to the target venous return site in the cephalic vein 14 until venous access is attained. A guidewire 36 is then advanced through the crossing needle 34 and into the vein 14. Following this, the crossing needle 34 is removed. In exemplary embodiments, the crossing needle 34 may be a crossing needle sold under the trademark ELLIPSYS® by Avenu Medical, Inc., the assignee of the present application.

Figure 20:
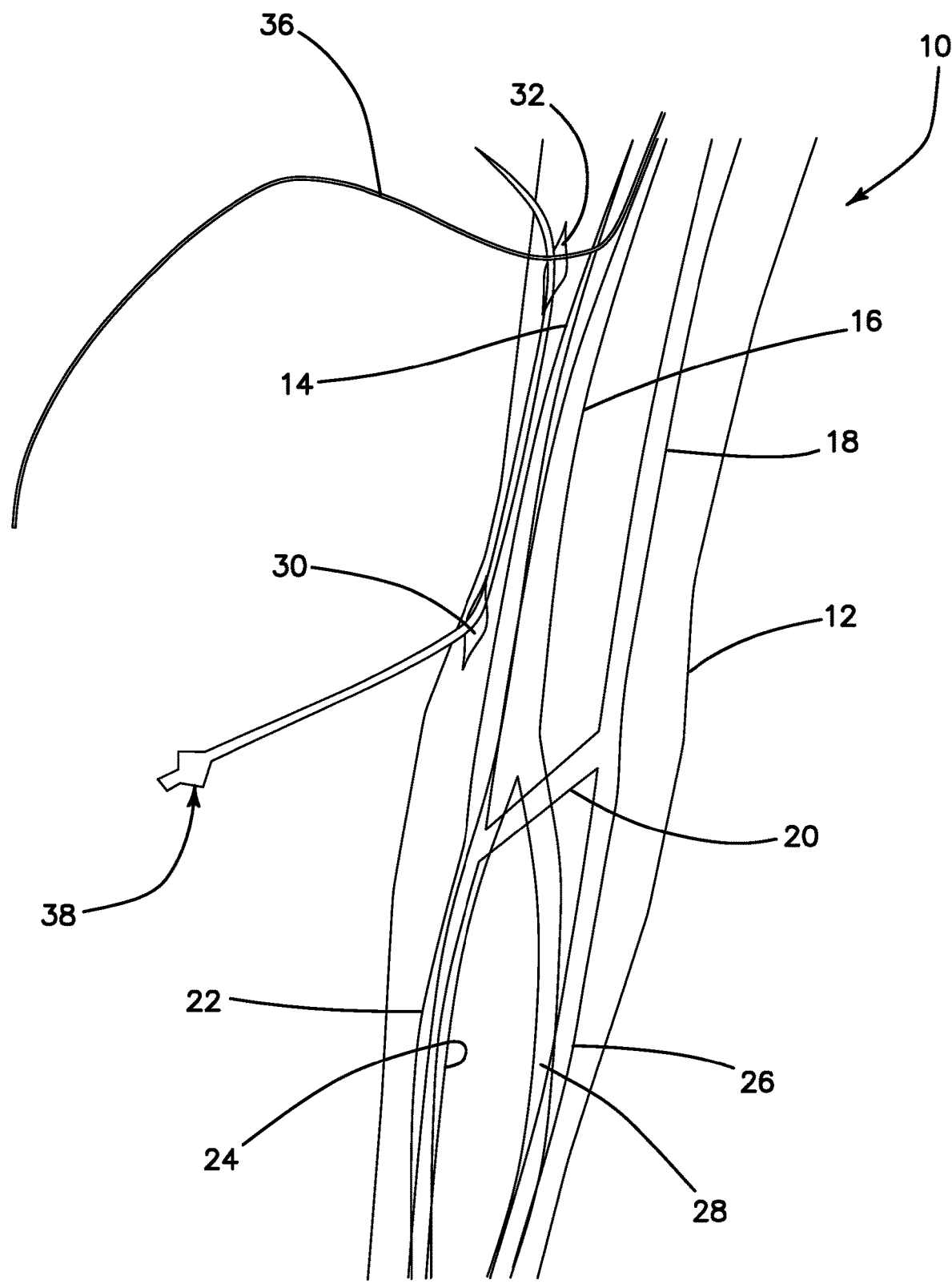
FIG. 20 is a schematic representation similar to FIGS. 18-19, illustrating additional steps according to the modified exemplary method.
Figure 21:
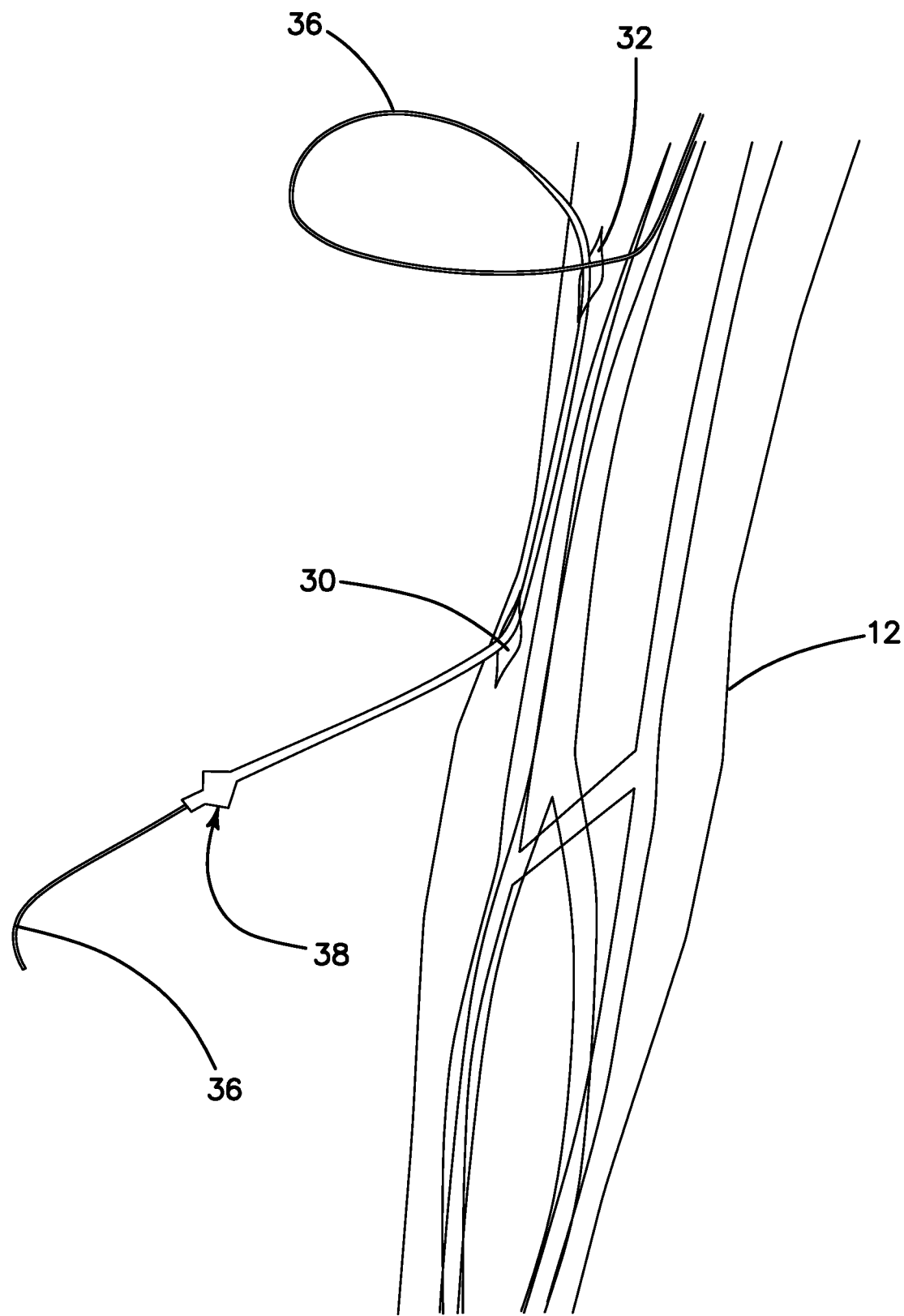
FIG. 21 is a schematic representation similar to FIGS. 18-20, illustrating additional steps according to the modified exemplary method.
Figure 22:
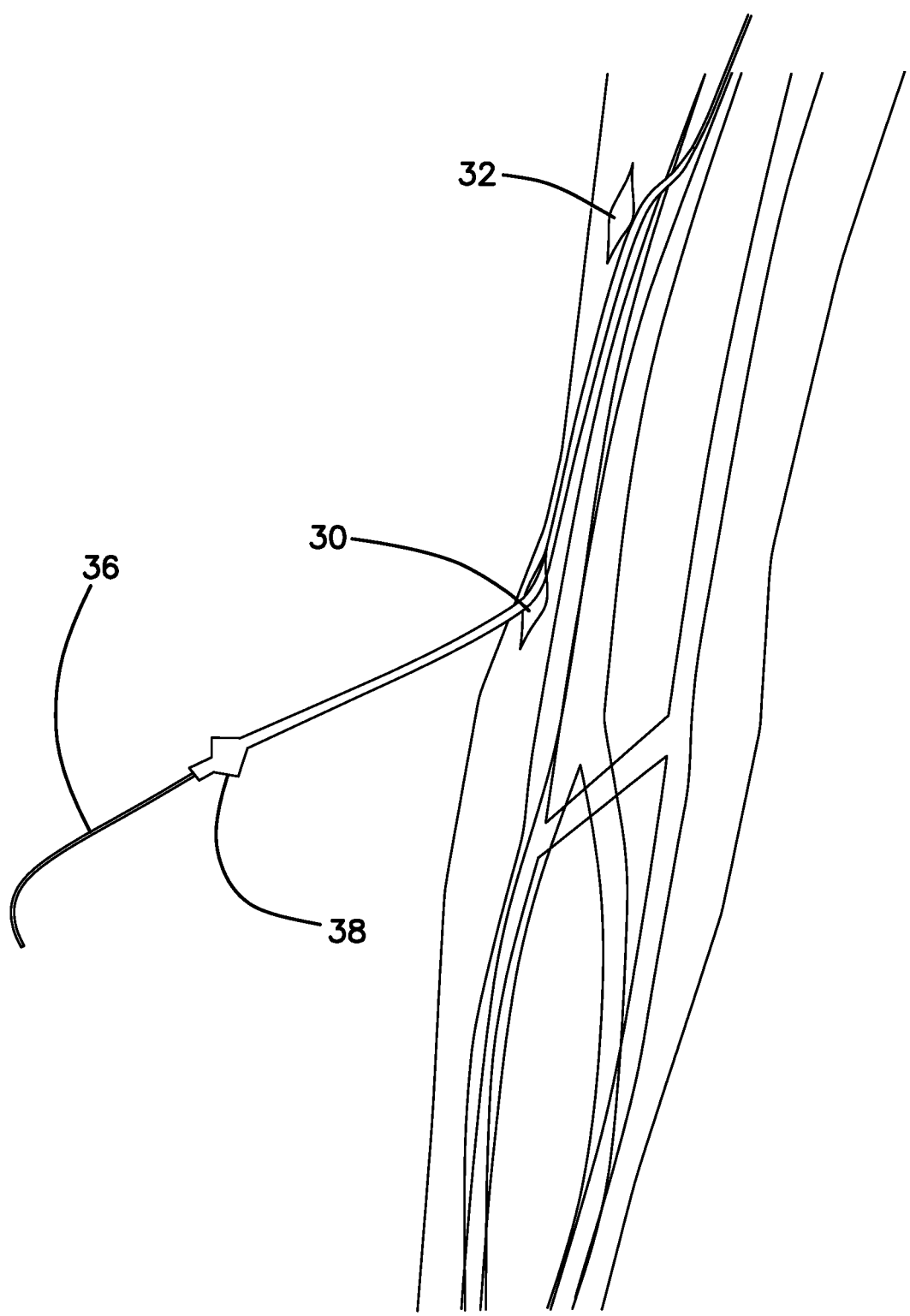
FIG. 22 is a schematic representation similar to FIGS. 18-21, illustrating additional steps according to the modified exemplary method.

As shown in FIG. 20, blunt dissection from the second incision 32 to the first incision 30 is performed with imaging guidance, such as ultrasound. A first tear-away sheath 38 is then placed from the first incision 30 to the second incision 32. The guidewire 36 is then back-loaded through the sheath 38, as shown in FIG. 21. The sheath 38 is then repositioned over the guidewire 36 and advanced into the target venous return site (FIG. 22).

Figure 23:
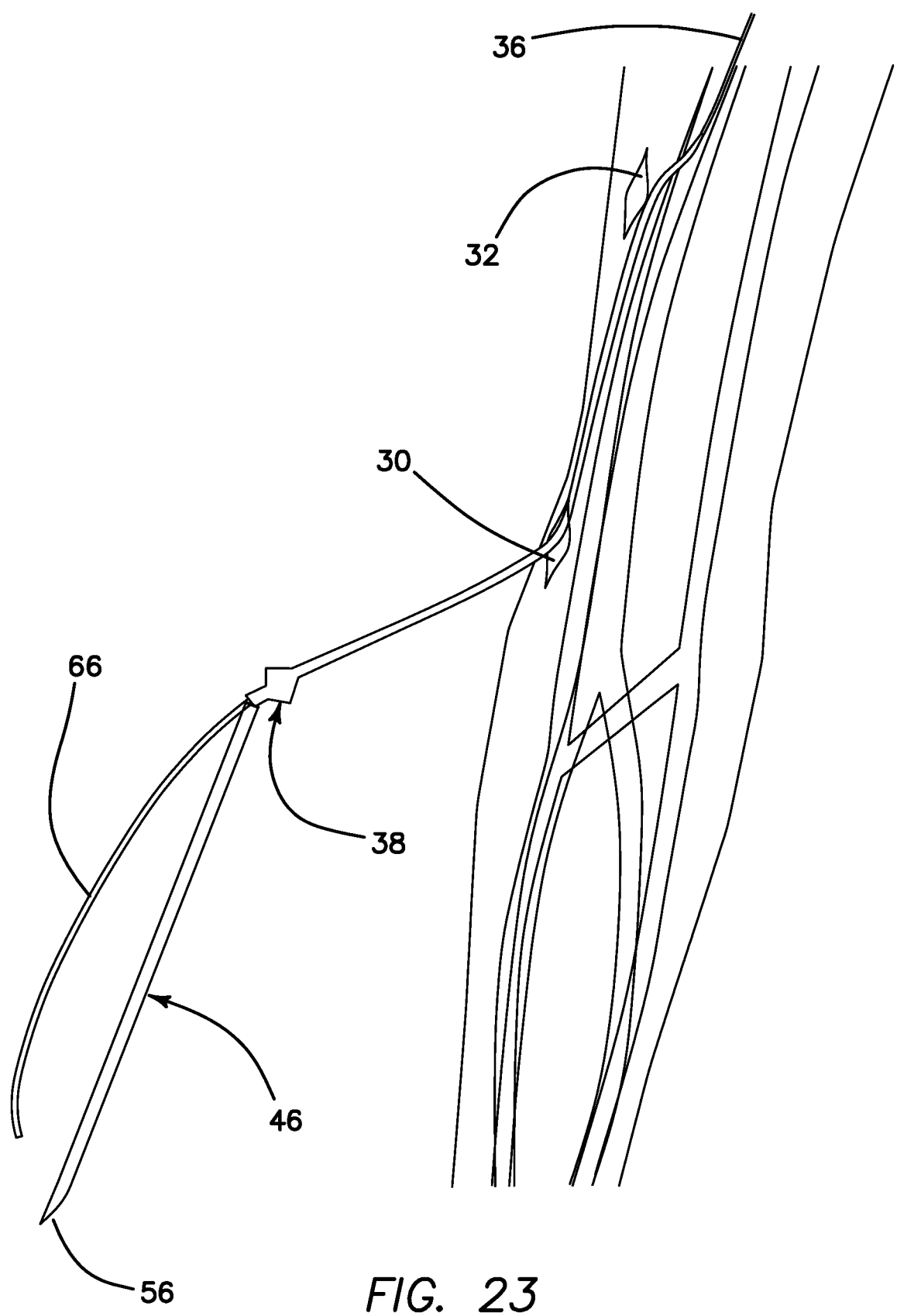
FIG. 23 is a schematic representation similar to FIGS. 18-22, illustrating additional steps according to the modified exemplary method.

At this point, this exemplary second method diverges from the first method discussed above. As shown in FIG. 23, the open end of a biologic graft 46 can now be placed with the target venous return site with a push catheter 66 to be pushed over the guidewire 36, down the first tear-away sheath 38.

Figure 24:
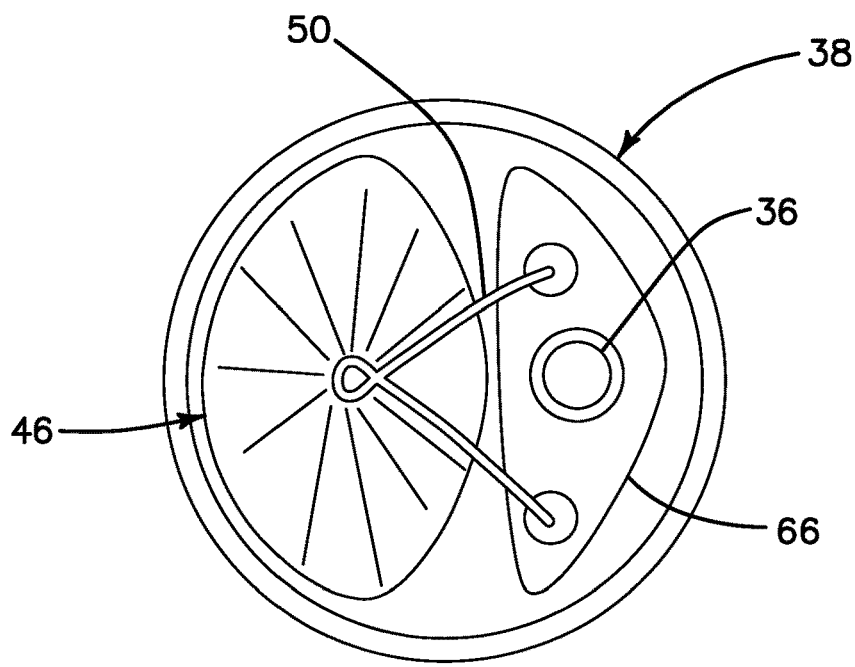
FIG. 24 is a cross-sectional view of a first sheath of an exemplary device of the invention, illustrated during performance of the step shown in FIG. 23.

FIG. 24 illustrates a cross-sectional view of the first sheath 38, showing a lumen A of the sheath 38, the push catheter 66 (B), the first guidewire 36 (C), and a ligature 50 (D) attached to the biologic graft 46 (E). In this embodiment, the push catheter 66 (B) may be a three lumen design, as illustrated, that enables the user to manipulate and/or extract the ligature 50 (D) during placement of the biologic graft 46 (E) within the target return vein.

Figure 25:
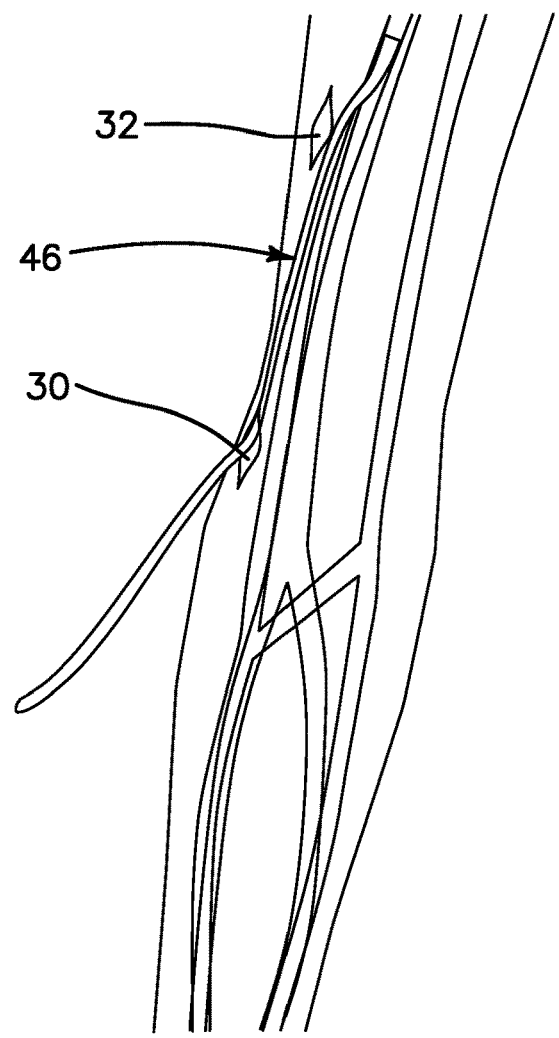
FIG. 25 is a schematic representation similar to FIGS. 18-23, illustrating the biologic graft positioned and attached to the target venous return site.
Figure 26:
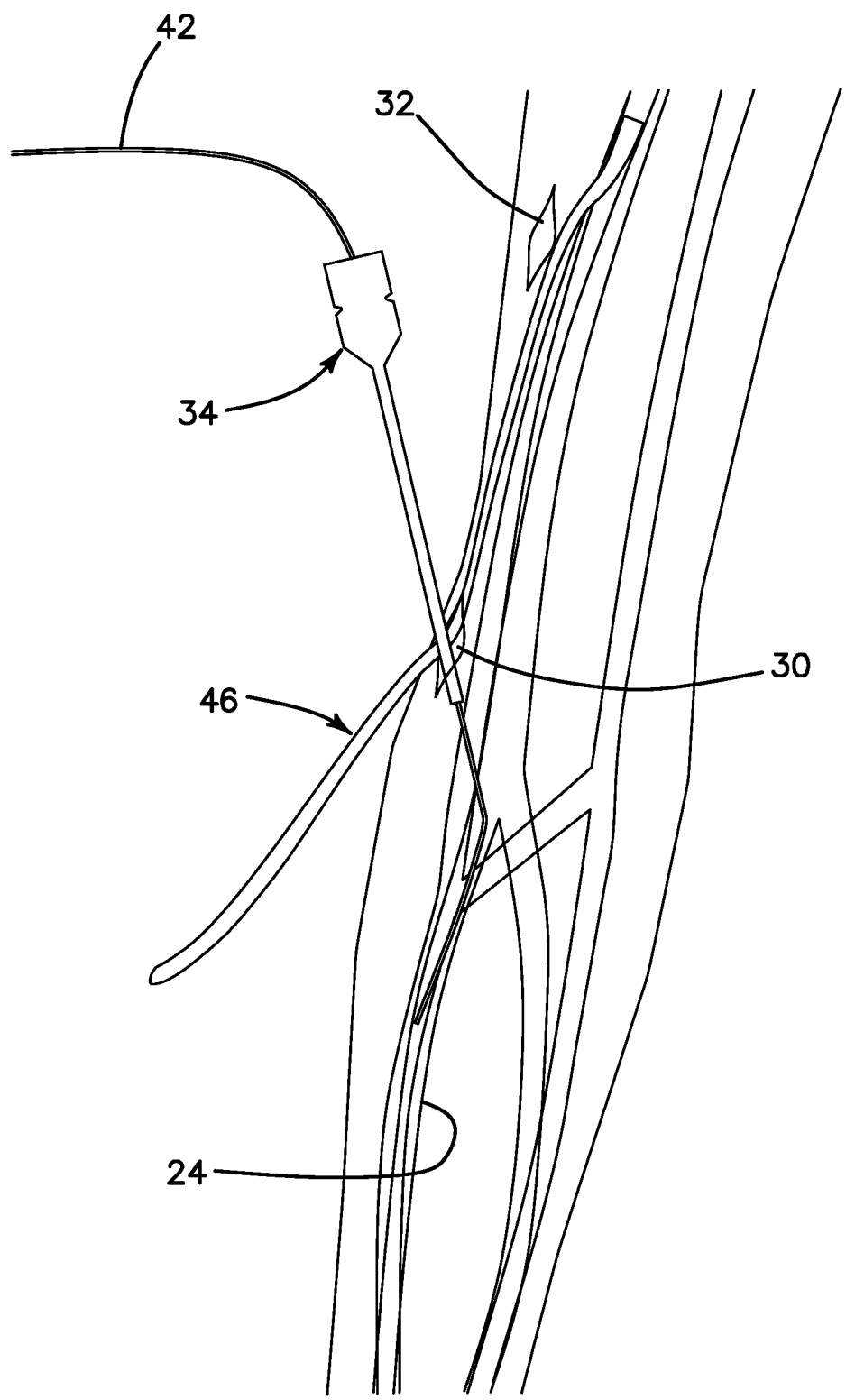
FIG. 26 is a schematic representation similar to FIGS. 18-23 and 25, illustrating additional steps according to the modified exemplary method.

FIG. 25 shows the biologic graft 46 positioned so as to be attached to the target venous return site.

Figure 27:
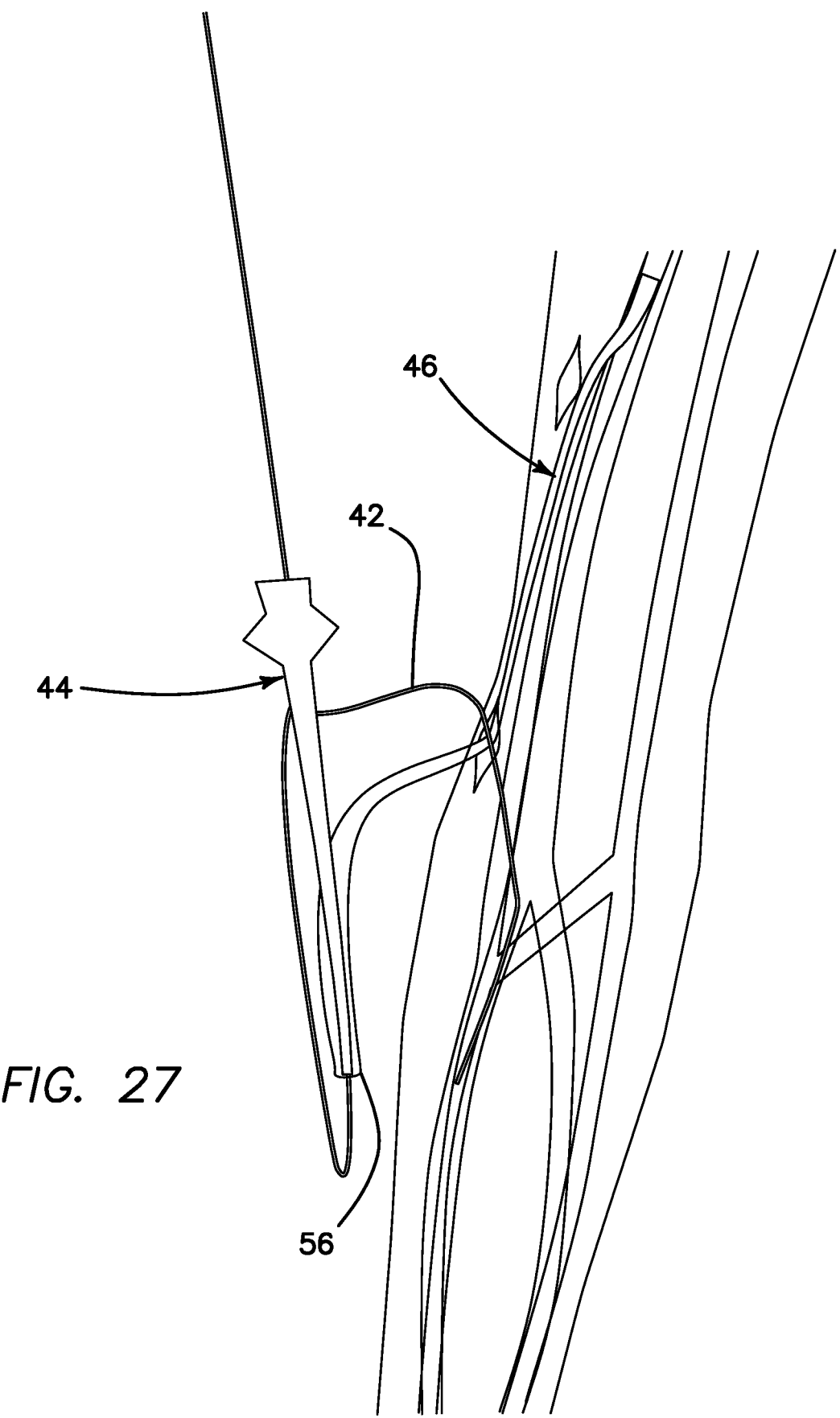
FIG. 27 is a schematic representation similar to FIGS. 18-23 and 25-26, illustrating additional steps according to the modified exemplary method.

At this juncture, a crossing needle 34, which may be a crossing needle sold under the trademark ELLIPSYS® by Avenu Medical, Inc., or similar device, is utilized, possibly under imaging guidance, such as ultrasound guidance, to gain arterial access at the desired fistula creation site and a second guidewire 42 is advanced into the target vessel 24. Blunt dissection can be performed next t or over the guidewire 42 to create a pathway for the biologic graft 46. As shown in FIG. 27, a puncture is then made in an appropriate location along the biologic graft 46 and a second sheath 44, which in an exemplary embodiment is a 6F x 10 cm sheath, is placed into the biologic graft 46. The proximal end of the second guidewire 42 is then poked through the closed end 56 of the biologic graft 46 and pushed through the sheath 44.

Figure 28:
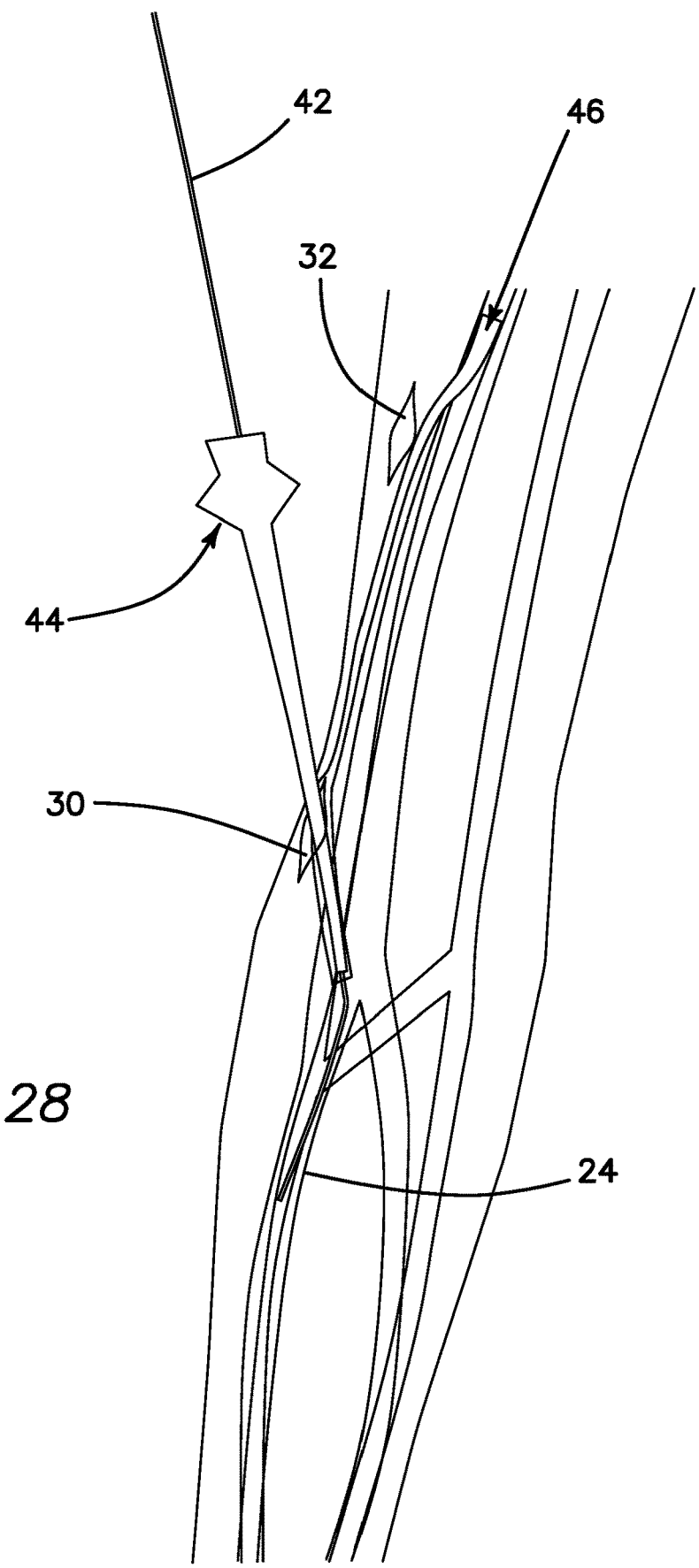
FIG. 28 is a schematic representation similar to FIGS. 18-23 and 25-27, illustrating additional steps according to the modified exemplary method.
Figure 29:
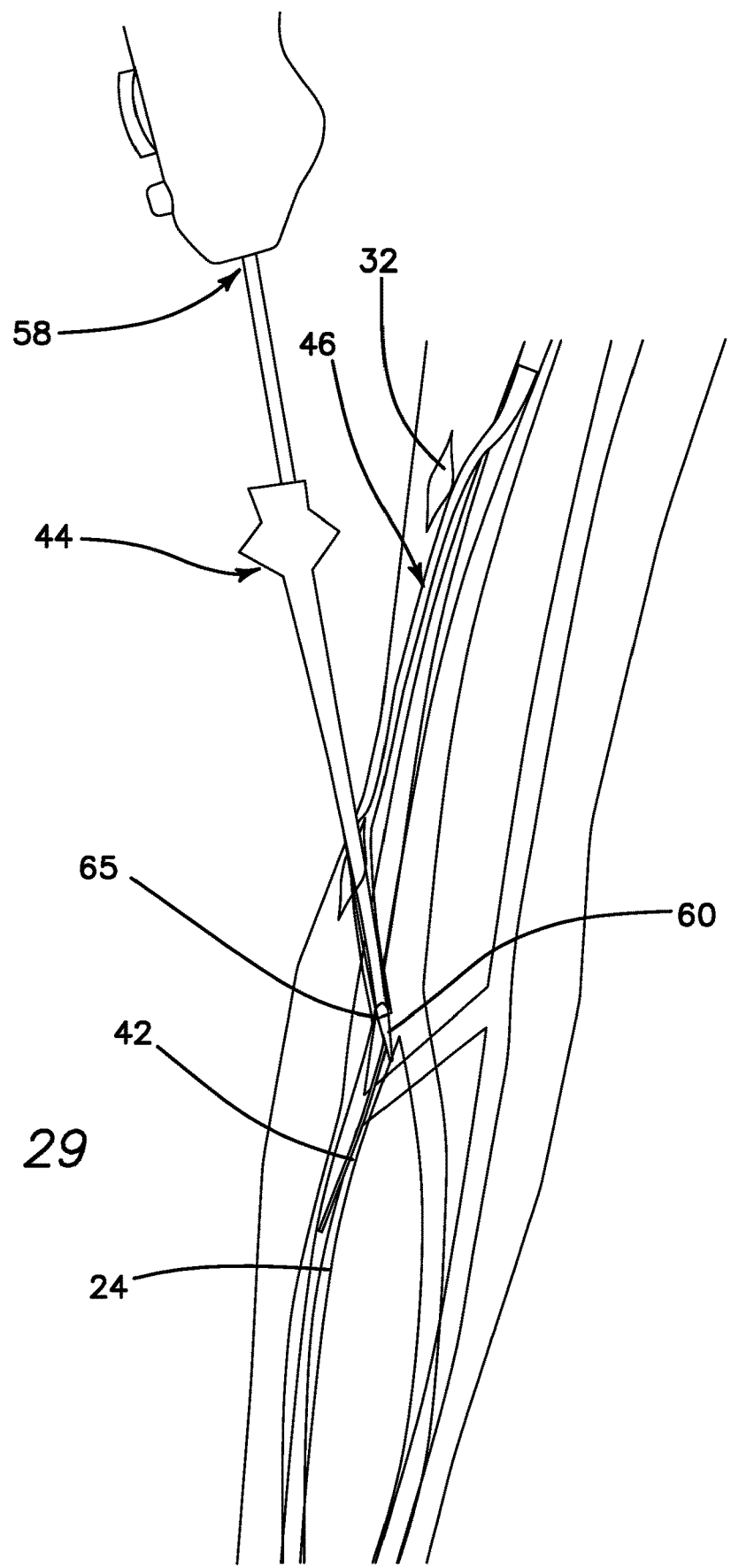
FIG. 29 is a schematic representation similar to FIGS. 18-23 and 25-28, illustrating additional steps according to the modified exemplary method.

As illustrated in FIG. 28, the biologic graft 46 can then be pushed into place near the target site using the second 6F sheath 44.

Figure 30:
FIG. 30 is a schematic representation similar to FIGS. 18-23 and 25-29, illustrating the completed procedure, with the biologic graft in place.

A catheter 58, which may be a catheter sold by the assignee of the present application, Avenu Medical, Inc., under the trademark ELLYPIS like that discussed above with respect to the embodiment of FIGS. 1-16, may then be positioned over the second guidewire 42 and a distal tip 60 of the catheter 58 is advanced through the closed end 56 of the biologic graft 46 and into the target artery 24. Once positioned, the catheter 58 is energized and an immediate and permanent anastomotic fusion 65 is created between the biologic graft 46 and the artery 24 (FIG. 29), again, as described with respect to the earlier embodiment. Once the anastomosis is created, the guidewire 42, sheath 44, and catheter 58 may be removed, leaving the biologic graft 46 in place, as shown in FIG. 30.

Accordingly, although an exemplary embodiment and method according to the invention have been shown and described, it is to be understood that all the terms used herein are descriptive rather than limiting, and that many changes, modifications, and substitutions may be made by one having ordinary skill in the art without departing from the spirit and scope of the invention.

What is claimed is:

1. A method of placing an arteriovenous graft in a patient, comprising:
   advancing a needle into a first blood vessel;
   advancing a guidewire through the needle and into the first blood vessel;
   removing the needle;
   performing a blunt dissection between two incisions;
   placing a first sheath between the two incisions;
   backloading the guidewire through the first sheath;
   advancing the first sheath into the first blood vessel over the guidewire;
   inserting a second guidewire into a second blood vessel;
   placing a second tear-away sheath over the second guidewire;
   advancing a biologic graft over the second guidewire into the second blood vessel at a biologic graft attachment site;
   advancing a catheter over the second guidewire;
   pushing a distal tip of the catheter through the biologic graft, a vessel wall of the second blood vessel, and into a lumen of the second blood vessel; and
   creating an anastomosis between the biologic graft and the second blood vessel by activating the catheter to apply energy to the vessel wall and to a wall of the biologic graft.

2. The method as recited in claim 1, wherein the first blood vessel is a vein and the second blood vessel is an artery.

3. The method as recited in claim 2, wherein the two incisions comprise first and second incisions, the first incision being disposed to access the vein and the second incision being disposed to access the artery.

4. The method as recited in claim 3, wherein the catheter comprises the distal tip and a proximal portion, each of the distal tip and the proximal portion having corresponding tissue contacting surfaces, wherein the distal tip pushing step includes pushing the distal tip distally relative to the catheter proximal portion, so that the tissue contacting surface of the distal tip is disposed in the lumen of the artery and the tissue contacting surface of the proximal portion is disposed proximally of the artery wall and the biologic graft wall.

5. The method as recited in claim 4, wherein the creating an anastomosis step comprises withdrawing the distal tip of the catheter proximally so that the artery wall and the biologic graft wall are clamped between the respective tissue contacting surfaces.

6. The method as recited in claim 5, wherein the activating the catheter step comprises energizing a thermal energy element disposed on at least one of the respective tissue contacting surfaces, the energized thermal energy element cutting the artery wall and the biologic graft wall to create the anastomosis between the artery and the biologic graft.

7. The method as recited in claim 6, and further comprising pushing the biologic graft distally into the vein.

8. The method as recited in claim 7, and further comprising placing the second sheath into the biologic graft, then poking a proximal end of the second guidewire through a closed end of the biologic graft and pushing the second guidewire through the second sheath.

9. The method as recited in claim 8, and further comprising pushing the biologic graft in place near the anastomosis site.

10. The method as recited in claim 2, and further comprising placing a ligature at the anastomosis site to secure the biologic graft and the artery and to maintain hemostasis.

11. The method as recited in claim 10, wherein the biologic graft comprises a tube sock biologic.

12. The method as recited in claim 11, wherein the step of advancing the biologic graft comprises placing the biologic graft over a third sheath.

13. The method as recited in claim 12, wherein the second guidewire is poked through a closed end of the tube sock biologic graft and through the third sheath.

14. The method as recited in claim 13, wherein the biologic graft and the third sheath are advanced through the second sheath into the artery at the biologic graft attachment site.

15. The method as recited in claim 14, wherein the ligature is placed at the anastomosis site by using a push catheter to push the ligature from an open end of the biologic graft distally to the anastomosis site.

16. A method of placing an arteriovenous graft in a patient, comprising:
   inserting a guidewire into a blood vessel;
   placing a sheath over the guidewire;
   advancing a biologic graft over the guidewire into the blood vessel at a biologic graft attachment site;
   advancing a catheter over the guidewire;
   pushing a distal tip of the catheter through the biologic graft, a vessel wall of the blood vessel, and into a lumen of the blood vessel; and
   creating an anastomosis between the biologic graft and the blood vessel by activating the catheter to apply energy to the vessel wall and to a wall of the biologic graft.

17. The method as recited in claim 16, wherein the catheter comprises the distal tip and a proximal portion, each of the distal tip and the proximal portion having corresponding tissue contacting surfaces, wherein the distal tip pushing step includes pushing the distal tip distally relative to the catheter proximal portion, so that the tissue contacting surface of the distal tip is disposed in the lumen of the blood vessel and the tissue contacting surface of the proximal portion is disposed proximally of the vessel wall and the biologic graft wall.

18. The method as recited in claim 17, wherein the creating an anastomosis step comprises withdrawing the distal tip of the catheter proximally so that the artery wall and the biologic graft wall are clamped between the respective tissue contacting surfaces.

19. The method as recited in claim 18, wherein the activating the catheter step comprises energizing a thermal energy element disposed on at least one of the respective tissue contacting surfaces, the energized thermal energy element cutting the artery wall and the biologic graft wall to create the anastomosis between the artery and the biologic graft.

20. The method as recited in claim 17, and further comprising placing a ligature at the anastomosis site to secure the biologic graft and the artery and to maintain hemostasis.

* * * * *